US009061064B2

(12) United States Patent
Trieu

(10) Patent No.: US 9,061,064 B2
(45) Date of Patent: *Jun. 23, 2015

(54) IMPLANTABLE DEVICES FOR CHEMONUCLEOLYSIS OF INTERVERTEBRAL DISCS

(75) Inventor: Hai H. Trieu, Cordova, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 1777 days.

This patent is subject to a terminal disclaimer.

(21) Appl. No.: 11/605,815

(22) Filed: Nov. 29, 2006

(65) Prior Publication Data

US 2007/0128575 A1    Jun. 7, 2007

Related U.S. Application Data

(62) Division of application No. 10/634,798, filed on Aug. 6, 2003, now Pat. No. 7,169,405.

(51) Int. Cl.
| | | |
|---|---|---|
| *A61K 9/00* | (2006.01) | |
| *A61K 47/32* | (2006.01) | |
| *A61L 27/54* | (2006.01) | |
| *A61K 47/34* | (2006.01) | |
| *A61F 2/44* | (2006.01) | |
| *A61F 2/30* | (2006.01) | |

(52) U.S. Cl.
CPC ....... *A61K 47/32* (2013.01); *A61F 2002/30586* (2013.01); *A61F 2002/30677* (2013.01); *A61F 2002/444* (2013.01); *A61K 9/0024* (2013.01); *A61K 47/34* (2013.01); *A61L 27/54* (2013.01); *A61L 2300/254* (2013.01); *A61L 2300/414* (2013.01); *A61L 2300/45* (2013.01); *A61L 2300/602* (2013.01); *A61L 2300/622* (2013.01); *A61L 2430/38* (2013.01)

(58) Field of Classification Search
None
See application file for complete search history.

(56) References Cited

U.S. PATENT DOCUMENTS

| | | | |
|---|---|---|---|
| 3,320,131 A | | 5/1967 | Smith |
| 3,941,127 A | | 3/1976 | Froning |
| 3,964,480 A | | 6/1976 | Froning |
| 3,975,350 A | * | 8/1976 | Hudgin et al. ................. 524/108 |
| 4,039,682 A | | 8/1977 | Ausman et al. |
| 4,374,926 A | | 2/1983 | Stern |
| 4,430,760 A | | 2/1984 | Smestad |
| 4,439,423 A | | 3/1984 | Smith |
| 4,696,816 A | * | 9/1987 | Brown ........................ 424/94.65 |
| 4,719,108 A | * | 1/1988 | Smith .......................... 424/94.2 |
| 4,904,260 A | | 2/1990 | Ray et al. |
| 5,422,103 A | | 6/1995 | Stern et al. |
| 5,456,679 A | | 10/1995 | Balaban et al. |
| 5,468,480 A | | 11/1995 | Barrett et al. |
| 5,645,549 A | | 7/1997 | Boyd et al. |
| 5,919,235 A | * | 7/1999 | Husson et al. ............. 623/17.16 |
| 6,007,810 A | | 12/1999 | Ishikawa et al. |
| 6,063,378 A | | 5/2000 | Nohara et al. |
| 6,231,598 B1 | * | 5/2001 | Berry et al. ................... 623/1.15 |
| 6,231,615 B1 | | 5/2001 | Preissman |
| 6,280,475 B1 | | 8/2001 | Bao et al. |
| 6,294,187 B1 | | 9/2001 | Boyce et al. |
| 6,471,688 B1 | | 10/2002 | Harper et al. |
| 6,491,666 B1 | | 12/2002 | Santini, Jr. et al. |
| 6,527,762 B1 | | 3/2003 | Santini, Jr. et al. |
| 6,537,256 B2 | | 3/2003 | Santini, Jr. et al. |
| 6,551,838 B2 | | 4/2003 | Santini, Jr. et al. |
| 6,656,162 B2 | | 12/2003 | Santini, Jr. et al. |
| 6,669,683 B2 | | 12/2003 | Santini, Jr. et al. |
| 6,773,429 B2 | | 8/2004 | Sheppard, Jr. et al. |
| 6,827,250 B2 | | 12/2004 | Uhland et al. |
| 6,849,463 B2 | | 2/2005 | Santini, Jr. et al. |
| 6,973,718 B2 | | 12/2005 | Sheppard, Jr. et al. |
| 6,976,982 B2 | | 12/2005 | Santini, Jr. et al. |
| 7,014,636 B2 | | 3/2006 | Gilbert |
| 7,163,545 B2 | * | 1/2007 | Yaszemski et al. ........... 606/152 |
| 7,217,293 B2 | | 5/2007 | Branch, Jr. |
| 2001/0020188 A1 | | 9/2001 | Sander |
| 2002/0026244 A1 | * | 2/2002 | Trieu ......................... 623/17.16 |
| 2002/0029083 A1 | | 3/2002 | Zucherman et al. |
| 2002/0087113 A1 | | 7/2002 | Hartlaub |
| 2002/0106362 A1 | * | 8/2002 | Masuda et al. ............... 424/94.6 |
| 2002/0116005 A1 | * | 8/2002 | Storer et al. .................... 606/92 |
| 2002/0128202 A1 | | 9/2002 | Carney et al. |

(Continued)

FOREIGN PATENT DOCUMENTS

| | | |
|---|---|---|
| WO | 9634093 A1 | 10/1996 |
| WO | 0145577 A2 | 6/2001 |

(Continued)

OTHER PUBLICATIONS

Chymopapain from GenBank Accession No. CAA66378, pp. 1-2. Accessed May 14, 2009.*
Collagenase from GenBank Accession No. CAA07432, pp. 1-3. Accessed May 14, 2009.*
Fibroblast growth factor from GenBank Accession No. CAA41788, pp. 1-2. Accessed May 14, 2009.*
Morphogenetic protein from GenBank Accession No. NP_391488, pp. 1-3. Accessed May 14, 2009.*
Albumin from GenBank Accession No. CAA00606, pp. 1-2. Accessed May 14, 2009.*
Sigma Product Information for Chymopapain, C 8526 (Oct. 2003).*
SigmaAldrich Chymopapain (C 8526) Product Excerpt (2013) from the Sigma-Aldrich online catalog, www.sigmaaldrich.com.*

(Continued)

*Primary Examiner* — Karlheinz R Skowronek
*Assistant Examiner* — Joseph Fischer
(74) *Attorney, Agent, or Firm* — Sorell Lenna & Schmidt LLP

(57) ABSTRACT

Devices for the treatment of intervertebral discs are described. The devices, when implanted into the nucleus pulposus of an intervertebral disc, provide for the controlled release of active agents into the disc. The active agent can be a chemonucleolytic agent such as chymopapain. The device can also comprise one or more binders. The device can be an elongate solid body having a tapered or rounded insertion end. Alternatively, the device can include a plurality of particles.

29 Claims, 22 Drawing Sheets

(56) References Cited

U.S. PATENT DOCUMENTS

| | | |
|---|---|---|
| 2002/0173851 A1 | 11/2002 | McKay |
| 2003/0009235 A1 | 1/2003 | Manrique et al. |
| 2003/0039676 A1 | 2/2003 | Boyce et al. |
| 2004/0010224 A1* | 1/2004 | Bodmeier .................. 604/82 |
| 2004/0031666 A1 | 2/2004 | Ostman |
| 2004/0091540 A1 | 5/2004 | Desrosiers et al. |
| 2004/0121486 A1 | 6/2004 | Uhland et al. |
| 2004/0133280 A1 | 7/2004 | Trieu |
| 2004/0143242 A1 | 7/2004 | Ludin et al. |
| 2004/0220552 A1 | 11/2004 | Heruth et al. |
| 2005/0031666 A1 | 2/2005 | Trieu |
| 2005/0070778 A1 | 3/2005 | Lackey et al. |
| 2005/0071009 A1 | 3/2005 | Muhanna et al. |
| 2006/0004456 A1 | 1/2006 | McKay |
| 2006/0046961 A1 | 3/2006 | McKay et al. |
| 2006/0047341 A1 | 3/2006 | Trieu |
| 2006/0240064 A9 | 10/2006 | Hunter et al. |
| 2007/0003598 A1 | 1/2007 | Trieu |
| 2007/0122446 A1 | 5/2007 | Trieu |
| 2007/0128575 A1 | 6/2007 | Trieu |
| 2007/0250044 A1 | 10/2007 | Trieu |
| 2007/0250046 A1 | 10/2007 | Trieu |
| 2007/0276337 A1 | 11/2007 | Trieu |

FOREIGN PATENT DOCUMENTS

| | | | |
|---|---|---|---|
| WO | WO01/45577 | A2 | 6/2001 |
| WO | 0217824 | A2 | 3/2002 |
| WO | WO02/17824 | A2 | 3/2002 |
| WO | 03068149 | A2 | 8/2003 |
| WO | WO03/068149 | A2 | 8/2003 |
| WO | 2004101015 | A2 | 11/2004 |
| WO | 2005014071 | A1 | 2/2005 |
| WO | 200592249 | A1 | 10/2005 |
| WO | 2005102440 | A2 | 11/2005 |
| WO | 2005115438 | A1 | 12/2005 |
| WO | 2006017456 | A2 | 2/2006 |
| WO | 2007127548 | A2 | 11/2007 |
| WO | 2008030832 | A1 | 3/2008 |
| WO | 2008030963 | A1 | 3/2008 |

OTHER PUBLICATIONS

Langer, Controlled Release of Small Molecules and Polypeptides, in Current Communications in Molecular Biology—Therapeutic Peptides and Proteins, Formulation, Delivery and Targeting, 1989, pp. 113-118.*

Kato et al., Comparison of Tissue Reaction With Chondroitinase ABC and Chymopapain in Rabbits as the Basis of Clinical Application in Chemonucleolysis, Clin. Orthopedics and Related Rsch, 288, 294-302, 1998.*

Katzung et al. (Editors), Basic and Clinical Pharmacology, 11th Edition, 2009, selected pp. 37, 38 and 49.*

Gunter et al., Hydration Level Monitoring Using Embedded Piezoresistive Microcantilever Sensors, Medical Engineering & Physics 27 (2005) 215-220.

Sheikh H et al. 2009. In vivo intervertebral disc regeneration using stem cell-derived chondroprogenitors. J Neurosurg Spine 10: 265-272.

Bron JL et al. 2009. Repair, regenerative and supportive therapies of the annulus fibrosus: achievements and challenges. Eur Spine J 18: 301-313.

* cited by examiner (A)

(B)

(C)

(D)

(E)

IMPLANTABLE DEVICES FOR CHEMONUCLEOLYSIS OF INTERVERTEBRAL DISCS

CROSS-REFERENCE TO RELATED APPLICATIONS

The present application is a Divisional Application of U.S. application Ser. No. 10/634,798 entitled "Methods And Devices For The Treatment Of Intervertebral Discs" filed on Aug. 6, 2003, incorporated herein by reference in its entirety.

BACKGROUND

1. Technical Field

The present application relates generally to methods and devices for the treatment of intervertebral discs and, in particular, to controlled release devices comprising a chemonucleolysis agent or multiple active agents and to methods of treatment comprising implanting the devices into an intervertebral disc.

2. Background of Technology

The intervertebral discs are cartilaginous plates surrounded by a fibrous ring that lie between the vertebral bodies and serve to cushion them. Through degeneration, wear and tear, and trauma, the fibrous tissue (annulus fibrosus) constraining the soft disc material (nucleus pulposus) may tear or become compressed. This squeezing or protrusion of the disc has been called herniated disc ruptured disc, herniated nucleus pulposus, or prolapsed disc. The extruded nucleus pulposus may press on a spinal nerve which may result in nerve damage, pain, numbness, muscle weakness and even paralysis.

Common methods of providing relief for damaged intervertebral discs include surgical removal of all or a portion of the intervertebral disc followed by fusion of the adjacent vertebrae. Although fusion can eliminate certain of the aforementioned symptoms, the restricted motion of the fused segment increases the range of motion required of the adjoining intervertebral discs and can therefore enhance their degeneration. As an alternative to fusion, the disc can be replaced with a spacer designed to simulate healthy intervertebral disc motion. The materials from which these disc spacers are made (e.g., polymeric and metallic materials), however, may disintegrate in the body or break down under repeated stress over prolonged periods.

Accordingly, there still exists a need for improved devices and methods for the treatment of intervertebral discs.

SUMMARY OF THE INVENTION

An intervertebral disc implant comprising a chemonucleolysis agent in solid form is provided wherein the chemonucleolysis agent is capable of the proteolytic degradation of the nucleus pulposus of an intervertebral disc. The implant can be a solid body comprising the chemonucleolysis agent. The solid body can be an elongate solid body or a microsphere. The solid body can further comprise a binder. The binder can be a bioresorbable polymer. Alternatively, the implant can comprise a plurality of unconsolidated particles at least some of which comprise the chemonucleolysis agent. Exemplary chemonucleolysis agents include chymopapain or chondroitinase ABC.

DETAILED DESCRIPTION

Methods and devices for the localized delivery of active agents to an essentially intact intervertebral disc are provided. The disclosed methods of treatment do not require the surgical removal of disc tissues. The disclosed methods and devices can be used to treat various conditions of the intervertebral disc including, but not limited to, protrusion, herniation, discogenic pain, dehydration and degeneration. The implants incorporate one or more active agents. By using the implants, detrimental side effects typically associated with direct injection of an active agent in liquid form (including leakage and overdose) can be reduced or eliminated. Methods of incorporating one or more active agents into a compact implantable device are also provided.

The devices can be delivered into the nucleus pulposus through a small opening or aperture in the annulus fibrosus. Once implanted, the device can provide a controlled and/or sustained release of one or more active agents from the implanted device to the surrounding disc tissues.

According to one embodiment, the device can comprise an active agent and a inert binder or matrix material. The binder is preferably an inert material. The binder can be chosen to provide an implant with desired release characteristics.

The device can be of any size and shape suitable for implantation into the intervertebral disc space of a mammal. Preferably, the device is compact in cross-section for delivery to the disc space though a small opening or aperture. According to one embodiment of the invention, the device is an elongate solid body. The elongate solid body can, for example, be a rod having a rounded or tapered insertion end.

The proposed methods and devices offer several advantages and can be used for various treatments of the intervertebral disc. Exemplary treatments include, but are not limited to, chemonucleolysis, pain-management, disc repair, and disc regeneration.

Figure 1A:
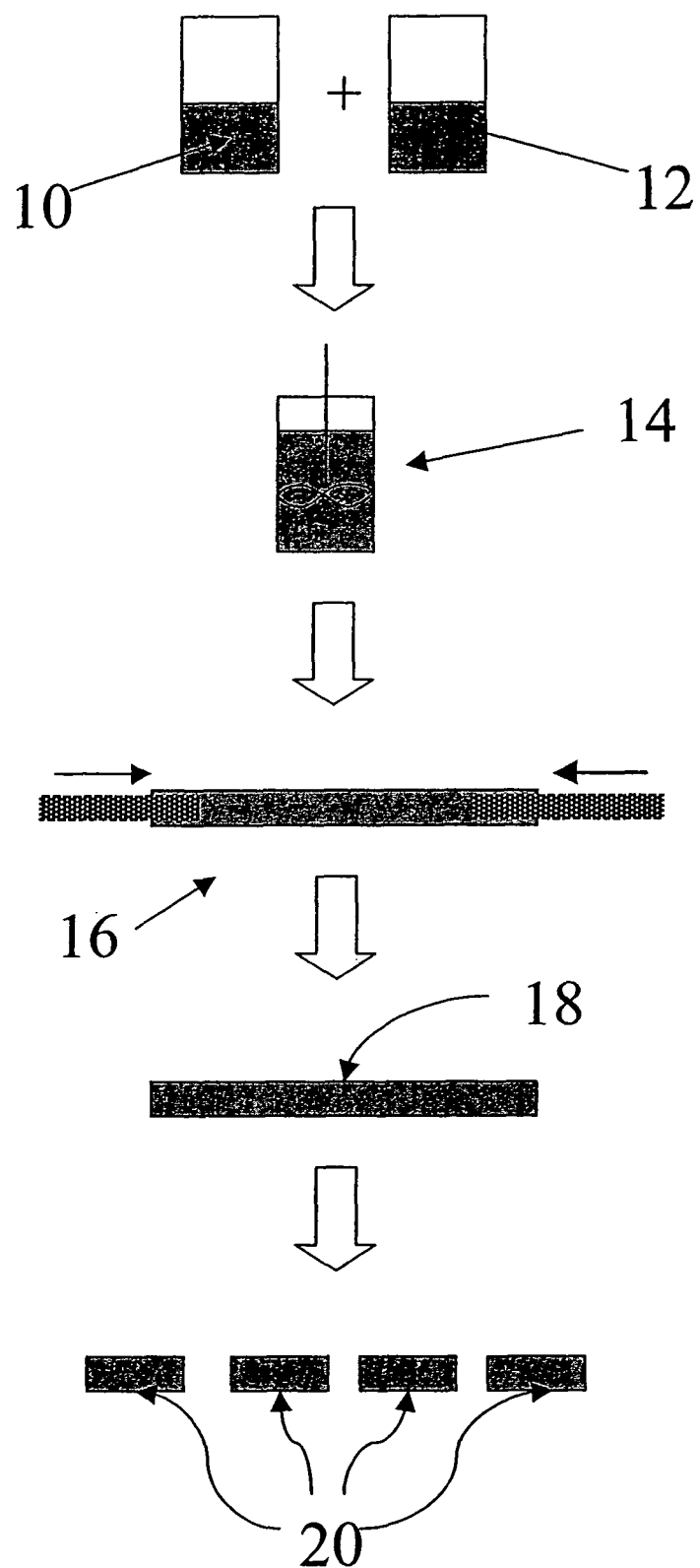
FIG. 1 illustrates two alternative methods of preparing an intervertebral disc implant.
Figure 1B:
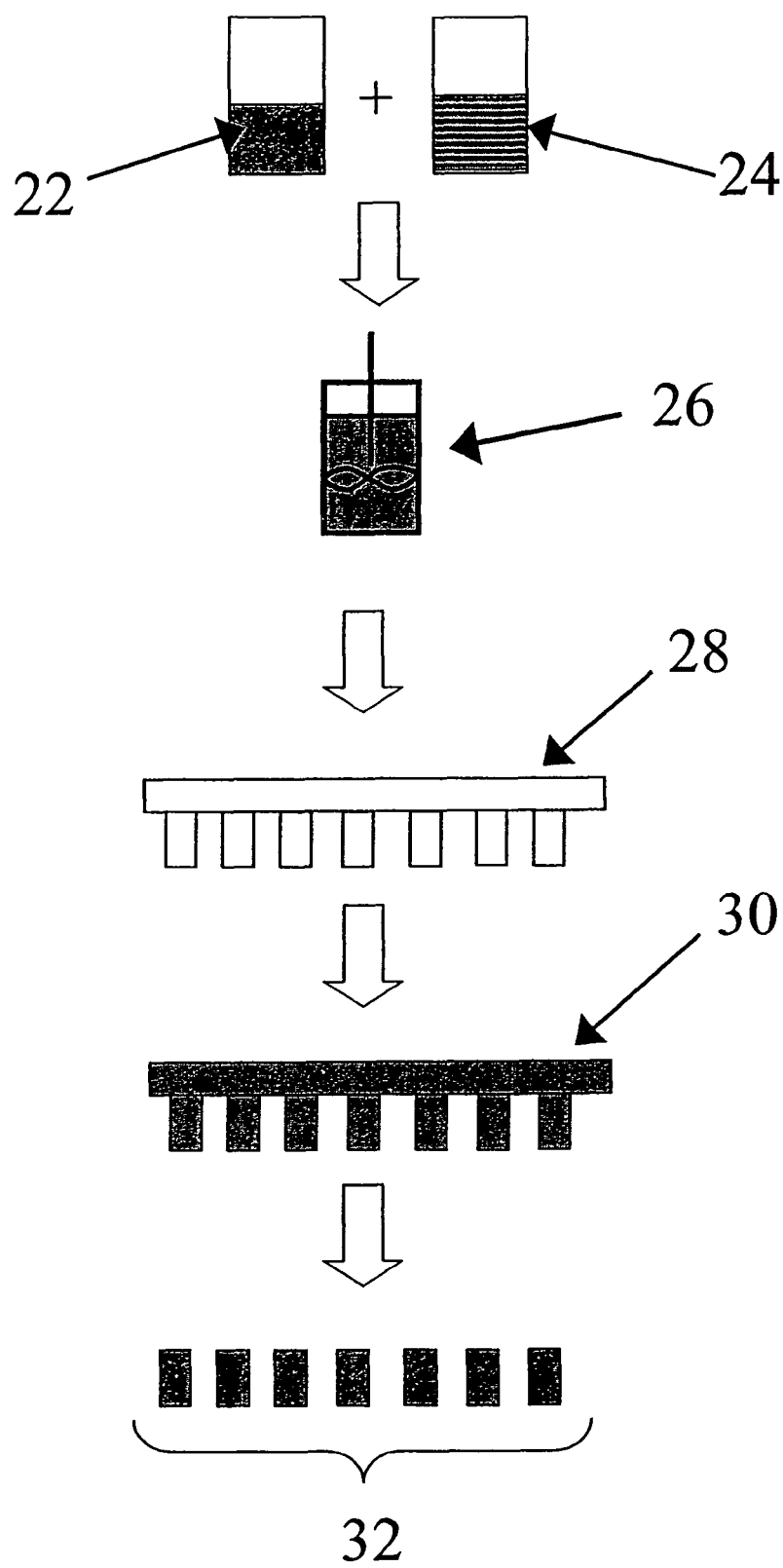

FIG. 1A illustrates two alternative methods of preparing an intervertebral disc implant. In a first method, an active agent 10 (e.g., a chemonucleolysis agent such as chymopapain) is mixed 14 with a binder 12 in an appropriate ratio. When the active agent 10 is chymopapain, the chymopapain in powder form can be mixed with the binder. The binder 12 can be a hygroscopic bioresorbable polymer. The active agent/binder mixture can then be consolidated under pressure and/or heat 16 into elongated rods 18. According to a preferred embodiment, the elongated rods can have a circular cross-section with a diameter of approximately 1 mm. Rods having a larger or smaller diameter can also be used.

In a second method of making an implant which is illustrated in FIG. I B, a mixture of an active agent and a binder 22 is combined with a solvent 24. The resulting solution is then mixed 26, and poured into a casting mold 28. The solvent 24 is then allowed to evaporate 30. The resulting casting can then be removed from the mold. As shown in FIG. I B, multiple devices 32 can be obtained from the mold.

In the above described methods, the concentration or quantity of chymopapain per unit length of the rods can be determined from the manufacturing process. For example, the amount of active agent (e.g., chymopapain) in an implant can be determined from the ratio of active agent/binder in the mixture and from the volume or weight of the implant. The appropriate length of rod can then be chosen to achieve the desired dosage.

The implant as described above can be used for the treatment of patients with a protruded disc and sciatica that meet the criteria for treatment using chemonucleolysis. Before implementing the method of treatment, the patient can be worked up as if he or she would receive an injection of chymopapain in solution.

A method of implanting a device as set forth above comprising a chemonucleolysis agent such as chymopapain is illustrated in FIGS. 2A-2H. For implantation of the device, a hypodermic needle or needle/trocar assembly (shown) of appropriate size 42 (e.g., having an inner diameter slightly larger than 1 mm) can be used as shown in FIG. 2A. As shown in FIG. 2B, the needle/trocar assembly can be inserted into the disc space between adjacent vertebrae 34, 36 until the needle tip passes through the outer and inner annulus fibrosis 38 to the center (i.e., the nucleus pulposus) of the intervertebral disc. Needle tip location can be verified using fluoroscopy. If a needle/trocar assembly is used, the needle 44 can then be removed leaving the hollow trocar 48 in position as shown in FIG. 2C. As shown in FIGS. 2D-2G, an appropriate length or lengths of implant 52 can then be inserted into the trocar and a stylet 50 can be used to push the length or lengths of rod 52 forward until it is deposited near the center of the nuclear disc space. Although a stylet is shown, a blunt needle or other pushing device can be employed. The trocar 48 and stylet 50 can then be removed and the implant(s) left behind within the nucleus pulposus as shown in FIG. 2H.

Figure 2:
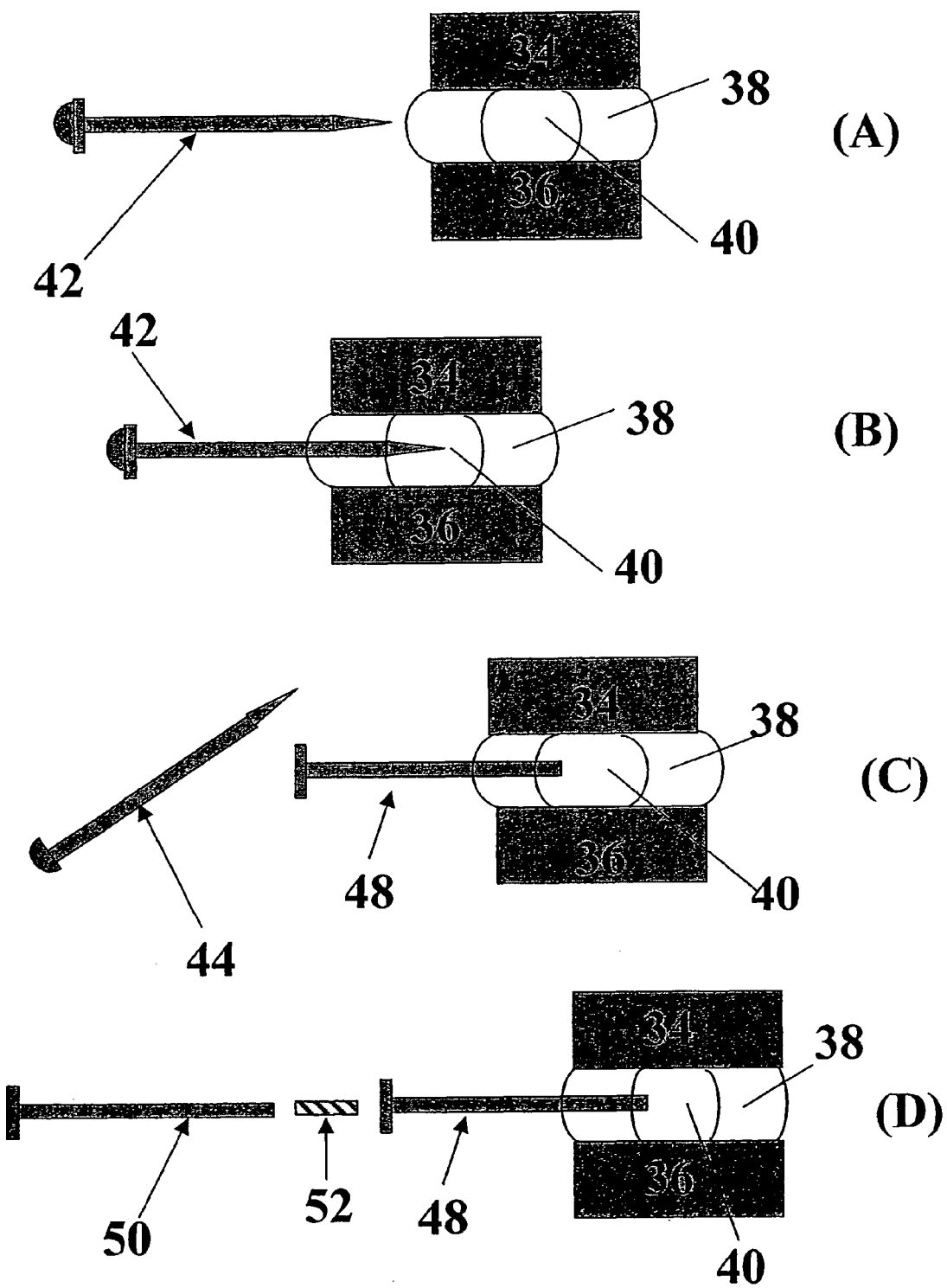
FIG. 2 illustrates a method of implanting an intervertebral disc implant as set forth in FIG. 1.
Figure 2:
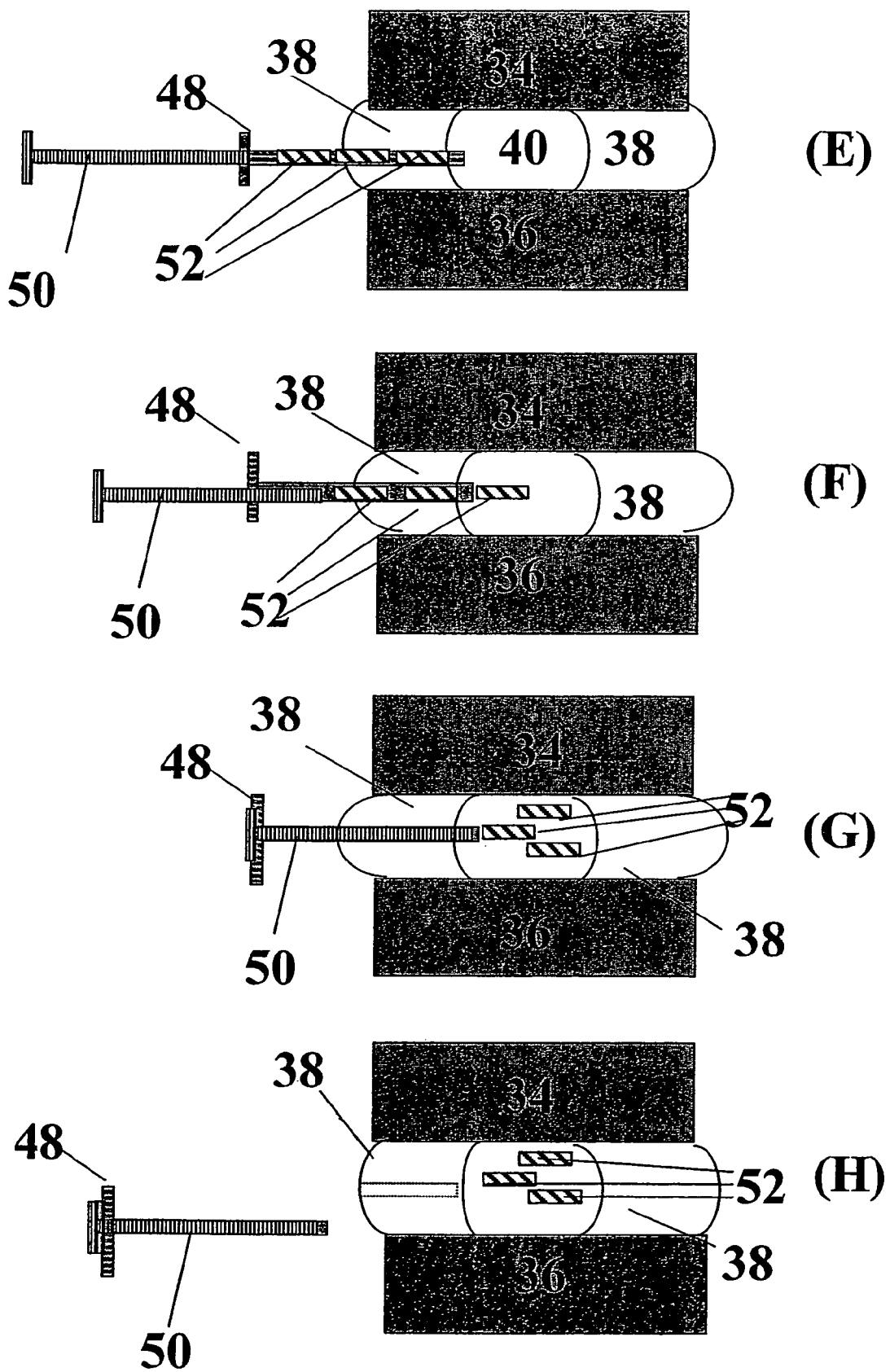
Figure 3:
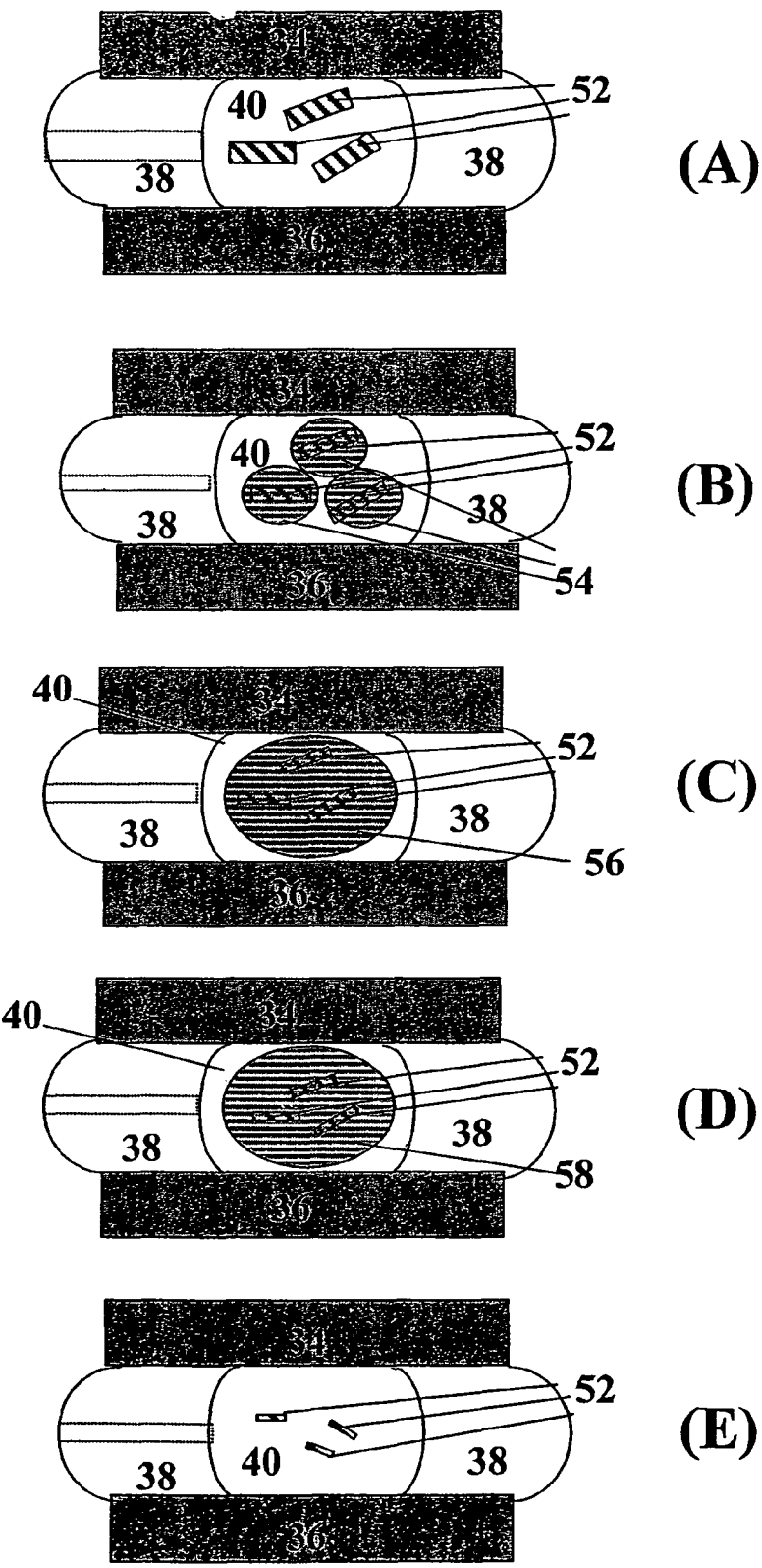
FIG. 3 illustrates the performance of an intervertebral disc implant as set forth in FIG. 1 after implantation into an intervertebral disc space.

In FIG. 2, three implants 52 are shown being implanted. However, more or fewer implants can be used to achieve the desired effect. The performance of a device comprising a chemonucleolysis agent such as chymopapain after implantation in a disc is illustrated in FIGS. 3A-3E. As shown in FIG. 3A, disc implants 52 (three shown) have been implanted into the nucleus pulposus 40 of an intervertebral disc. Once implanted, the hygroscopic polymer in the device can absorb water rapidly in the hydrated nucleus pulposus. As a result, the implant can swell up and release the chemonucleolysis agent 54, 56 58 to the surrounding disc tissues as shown in FIGS. 3B, 3C and 3D. The chymopapain released from the implant exerts a proteolytic action on the surrounding disc tissues. The implanted devices 52 are gradually eroded as shown in FIG. 3E and eventually disappear upon resorption.

The techniques and devices described herein provide a safe and effective means for various types of disc treatment including, but not limited to, chemonucleolysis, pain-management, repair, and regeneration. These techniques and devices also allow for the controlled and/or sustained release of desirable active agents within the disc. Further, the techniques and devices described herein can deliver an active agent to a localized area of the disc. For example, an implant comprising a chemonucleolysis agent such as chymopapain can be used to achieve localized degradation of the nucleus of an intervertebral disc without the destruction of other disc tissues including the annulus fibrosus. In this manner, reductions in the intradiscal pressure can be achieved using an implant comprising a chemonucleolysis agent. The aforementioned techniques and devices can also be used to avoid the potential side effects associated with the direct injection of a solution of an active agent including leakage or overdose. Therefore, the techniques and devices described herein can result in prolonged therapeutic effects while minimizing these and other adverse/side effects.

As set forth above, the devices can incorporate substances for chemonucleolysis such as chymopapain. The devices can also comprise pharmaceutical agents for therapeutic treatment. Exemplary pharmaceutical agents include, but are not limited to, steroids and pain medications. The device can also include growth factors and/or cells for disc repair or regeneration. Since many of these materials are currently in use, the risks of using a device comprising these active agents are reduced.

The implants described herein also provide for minimally invasive delivery or implantation. Moreover, the implants can be used to deliver an active agent to an essentially intact intervertebral discs. For example, by using the disclosed techniques, the surgical removal of disc tissues is not required. Additionally, the disclosed methods and devices can be used to treat various conditions of the disc (e.g. protrusion, herniation, discogenic pain, dehydration, degeneration, etc.) using appropriate active agents while minimizing the potential detrimental side effects typically associated with direct injection of active agents such as leakage or overdose.

Various means of incorporating active agents into a compact implantable device are provided. Methods for the delivery of the device into the nucleus of an intervertebral disc through a small annular opening are also provided. Once implanted, the devices allow for the controlled and/or sustained release of active agents the disc tissues surrounding the device.

According to a first embodiment, the device comprises at least two (2) materials: 1) an active agent (e.g., a therapeutic agent) and 2) a binder or matrix material. The binder is preferably an inert material. The device can be of any size and shape. The device is preferably compact in cross-section for delivery into the disc space though a small annular opening in the disc annulus.

The proposed methods and devices offer various advantages and can be used for various treatments of the ivt disc including, but not limited to, chemonucleolysis, pain-management, disc repair, and disc regeneration.

Set forth below are descriptions of various embodiments of devices comprising a single active agent and methods of using these devices to treat an intervertebral disc.

Embodiment 1

According to this embodiment, chymopapain in powder form is mixed with a hygroscopic bioresorbable polymer in appropriate ratio. The mixture is consolidated under pressure and/or heat into elongated rods with a diameter of approximately 1 mm. This device can be used for the treatment of patients with a protruded disc and/or sciatica that meet the criteria for chemonucleolysis. The patient can be worked up as if he or she would receive an injection of chymopapain solution. For implantation, a hypodermic needle of an appropriate size (e.g., having an inner diameter slightly larger than the device outer diameter) can be inserted into the disc space until the needle tip passes through the outer and inner annulus fibrosis to the center of the disc. The needle tip location can be verified using fluoroscopy. An appropriate length of implant is then inserted into the needle and a stylet is used to push the rod forward until it is deposited near the center of the nuclear disc space. The needle is then removed and the implant is left behind within the nucleus pulposus. As the hygroscopic polymer absorbs water rapidly in a hydrated nucleus pulposus, the rod swells up and releases chymopapain to surrounding disc tissues for proteolytic action. The device is gradually eroded and eventually disappears upon resorption.

Embodiment 2

According to this embodiment, pain medication in powder form is mixed with a bioresorbable polymer in an appropriate ratio. The mixture is consolidated under pressure and/or heat into elongated rods with a diameter of approximately 1 mm. This device is proposed for treatment of patients with discogentic pain.

For treatment, the patient can be worked up as if he or she would receive an injection of pain medication in liquid form. A hypodermic needle with appropriate size (e.g., an inner diameter slightly larger than the outer diameter of the implant) is inserted into the disc space until the needle tip passes through the outer and inner annulus fibrosis to the center. Needle tip location can be verified using fluoroscopy. An appropriate length or lengths of implant is then inserted into the needle and a stylet or other pushing device is used to push the implant forward until it is deposited near the center of the nuclear disc space. The needle is then removed and the implant is left behind within the nucleus pulposus. As the polymer and pain medication absorb water, the rod gradually releases pain medication to surrounding disc tissues for pain relief. The polymer gradually degrades and eventually disappears upon resorption, which occurs after the medication is depleted.

Embodiment 3

According to this embodiment, growth factors in powder form are mixed with a natural bioresorbable polymer in an appropriate ratio. The mixture is then consolidated under pressure into elongated rods with a diameter of approximately 1 mm. Other techniques for incorporating active agents such as growth factors in powder form into an inert binder are well known in the drug delivery industry and can be used to manufacture the implants. The concentration or quantity of growth factors per unit length of the rods can be determined from the active agent/binder ratio used in manufacturing the implant and from the dimensions of the implant.

This embodiment of the device is proposed for treatment of patients with a mild to moderately degenerated disc (i.e., a black disc). For implantation, a hypodermic needle with appropriate size (e.g., an inner diameter slightly larger than the outer diameter of the implant) is inserted into the disc space until the needle tip passes through the outer and inner annulus fibrosis to the nucleus pulposus. Needle tip location can be verified using fluoroscopy. An appropriate length of implant is then inserted into the needle and a stylet or other pushing device (e.g., a blunt needle) is used to push the implant forward until it is deposited near the center of the nuclear disc space. The needle is then removed and the implant is left behind within the nucleus pulposus. As the polymer and growth factors in the implant absorbs water, the rod swells up, begins erosion and gradually releases growth factors to surrounding disc tissues for disc repair or regeneration.

Embodiment 4

This embodiment involves the use of microspheres comprising an active agent. According to this embodiment, chymopapain is incorporated into microspheres comprising a binder (e.g., a hygroscopic bioresorbable polymer) at a desired ratio using methods known in the drug delivery industry. The concentration or quantity of chymopapain per unit weight of microsphere can be determined from the ratio of active agent to binder. This device is proposed for the treatment of patients with a herniated disc and sciatica that meet the criteria for treatment with chemonucleolysis.

Figure 9:
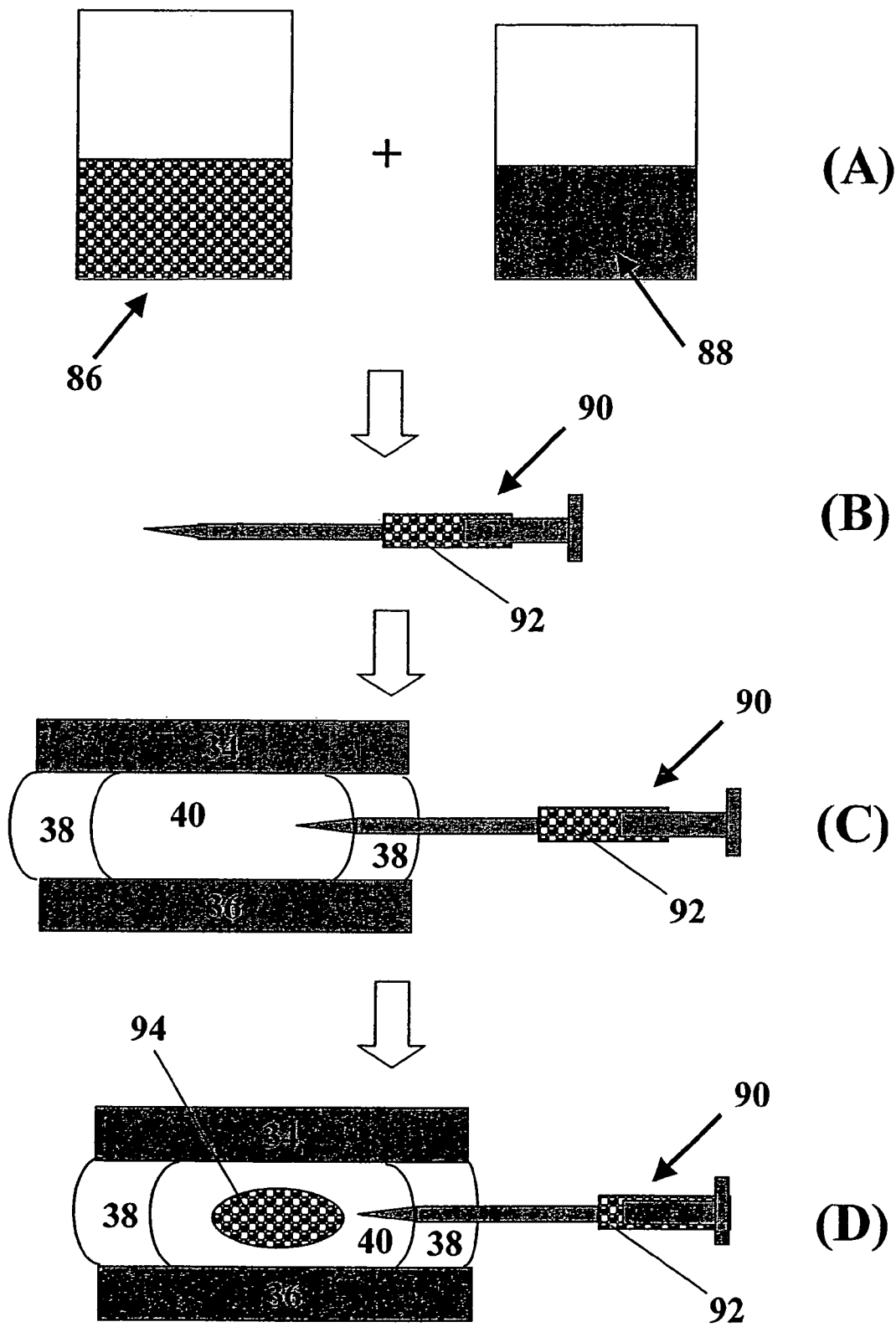
FIG. 9 illustrates a method of treating an intervertebral disc wherein microspheres comprising a chemonucleolysis agent as shown in FIG. 8 are mixed in liquid solution and injected into an intervertebral disc space.

A method of using the above described device is illustrated in FIGS. 9A-9D. For treatment, the patient can be worked up as if he or she would receive an injection of chymopapain in solution. The microspheres 86 can be mixed with a solvent 88 such as saline (FIG. 9A) and placed in a delivery device 90 (FIG. 9B). A syringe connected to a hypodermic needle of appropriate diameter is shown. The needle of the delivery device 90 can then be inserted into the disc space until the needle tip is located near the center of the nucleus pulposus 40 (FIG. 9C). Needle tip location can be verified using fluoroscopy. An appropriate quantity of microspheres 86 dispersed in solvent 88 can then be injected into the center of the disc (FIG. 9D). The needle is then removed (not shown) and the microspheres are left behind within the nucleus pulposus 40. As the polymer binder and chymopapain absorb water in the nucleus pulposus 40, the microspheres swell up, begin erosion and gradually release chymopapain to surrounding disc tissues for proteolytic action.

Embodiment 5

This embodiment is similar to Embodiment 2 except that the microspheres described in Embodiment 4 are used as an implant.

Embodiment 6

This embodiment is similar to Embodiment 3 except that the microspheres described in Embodiment 4 are used as an implant.

Embodiments 7-9

These embodiments are similar to Embodiments 1-3 except that implants comprising non-resorbable hydrogel polymer binders instead of resorbable polymer binders are used.

Embodiments 10-12

These embodiments are similar to Embodiments 1-3 except that implants comprising non-resorbable non-hydrogel polymer binders instead of resorbable polymer binders are used. According to further embodiments of the invention, methods and devices for the treatment multiple conditions of the disc (e.g. protrusion, herniation, discogenic pain, dehydration, degeneration, etc.) either simultaneously or sequentially are provided. These devices and methods can also be used to minimize the potential side effects typically associated with the direct injection of active agents in solution form to the intervertebral disc such as leakage, overdose, or drug interactions.

Various methods of incorporating more than one active agent (e.g., a chemonucleolysis agent, a pain medication, and/or a growth factor) into a compact implantable device are provided. Also provided are methods for the delivery of the device into the nucleus disc space through a small annular opening. Once implanted, the device can exhibit controlled and/or sustained release of multiple active agents at different rates and/or time points from the device to the surrounding disc tissues.

According to a further embodiment, when a growth factor is included in the device, various types of cells can be injected into the disc space during the growth factor releasing phase of the device in order to promote disc repair and regeneration.

As set forth above, the devices can comprise at least two different active agents (e.g., therapeutic substances) and one or more different binders or matrix materials. The device can be of any size and shape, but is preferably compact in cross-section for delivery to the disc space though a small annular opening.

The proposed methods and devices offer several advantages and can be applied for multiple treatments of the disc either simultaneously or sequentially (e.g. chemonucleolysis, pain-management, repair, regeneration, etc.)

The devices and methods described herein provide a safe and effective means for multiple types of disc treatment (e.g. chemonucleolysis, pain-management, repair, regeneration, etc.). The devices and methods can also provide for the controlled and/or sustained release of multiple active agents within the disc with a single implantation.

By using the techniques described herein, potential detrimental side effects associated with the injection of an active agent in solution can be avoided. These side effects include leakage, overdose and/or drug interactions. The devices and techniques described herein also allow for multiple therapeutic effects to be achieved either simultaneously or sequentially with one implantation while minimizing adverse/side effects.

The devices can incorporate any combination of two or more active agents. For example, the device can incorporate a combination of a chemonucleolysis agent (e.g., chymopapain or chondroitinase ABC), a pharmaceutical agent for therapeutic treatment (e.g., steroids and pain medication), a growth factor, and/or cells for disc repair or regeneration.

The risks involved in using the disclosed devices are reduced since similar active agents have been used in existing therapies. In addition, the devices and methods provide for minimally invasive delivery or implantation which can reduce discomfort to the patient during implantation and speed recovery.

Devices for the delivery of multiple active agents to an essentially intact intervertebral disc and methods of treatment using these devices are described herein. These methods of treatment do not require the surgical removal of disc tissue.

As set forth above, the devices can be used to treat multiple conditions of the disc simultaneously or sequentially. Exemplary conditions which can be treated include, but are not limited to, protrusion, herniation, discogenic pain, dehydration, and degeneration. The use of the devices for treatment can minimize the potential side effects typically associated with the direct injection of active agents in solution form such as leakage, overdose, or adverse drug interactions.

Various means of incorporating more than one active agent into a compact implantable device are provided. In addition, methods for the delivery of the device into the nucleus pulposus through a small annular opening are also provided. One implanted, the device can exhibit controlled and/or sustained release of active agents at different rates and/or time points from the device to surrounding disc tissues.

The device can comprise at least two different active agents (e.g., therapeutic substances) and one or more inert binders (matrix materials). For example, each of the active agents can be combined with a different binder to achieve a desired release profile for each active agent.

The device can be of any size and shape which can be implanted into an intervertebral disc. According to a preferred embodiment, the device is compact in cross-section for delivery to the disc space though a small annular opening in the annulus fibrosus of the disc.

The proposed methods and devices offer several advantages. In particular, the devices can be used to achieve multiple treatments of the disc simultaneously or sequentially (e.g. chemonucleolysis, pain-management, repair, regeneration, etc.).

Set forth below are various embodiments of devices comprising multiple active agents and methods of using these devices to treat an intervertebral disc.

Embodiment 13

Figure 4:
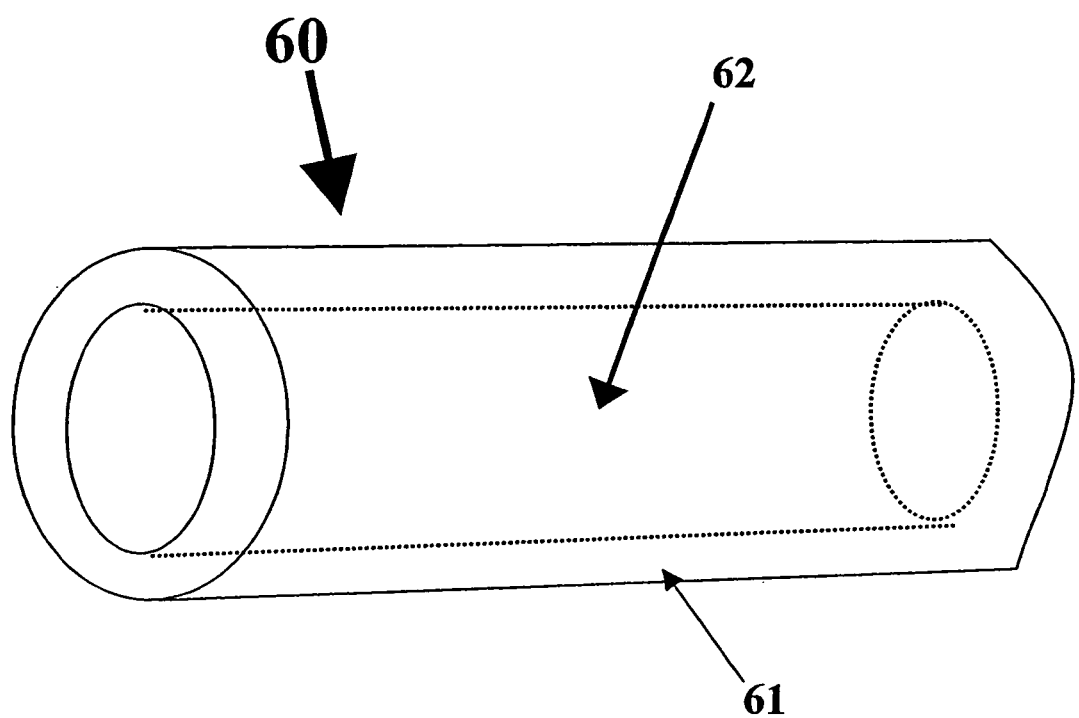
FIG. 4 shows an intervertebral disc implant for the delivery of multiple (i.e., two) active agents.

This device, which is depicted in FIG. 4, has an elongate solid body with a circular cross section. The device 60 includes a core 62 and a sheath 61. According to one embodiment, the core 62 comprises one or more growth factor and the sheath 61 comprises a chemonucleolysis agent (e.g., chymopapain).

The shell can also comprise a binder. For example, the binder can be a highly resorbable polymer which releases chymopapain quickly after implantation in the disc nucleus and therefore disappears within a short time (e.g. a few weeks) to expose the core 62 of the device. This phase of release is denoted release phase 1. In release phase 1, chemonucleolysis is accomplished with the quick release of the chemonucleolysis agent. The core can comprise a more slowly resorbable polymer. Once the core is exposed, the growth factors in the core can be released to stimulate disc cells to repair and/or regenerate the disc. This phase of release is denoted release phase 2. During release phase 2, various cells may be optionally injected into the disc space to accelerate the repair or regeneration process.

This device can be made using the following procedure. One or more growth factors are mixed with a first binder (e.g., a first bioresorbable polymer) and consolidated into a small diameter rod under pressure and/or heat. The resulting rod is subsequently coated with a mixture of a chemonucleolysis agent (e.g., chvmopapain) and a second bioresorbable polymer.

This device can be used for treatment of patients with a protruded disc and sciatica that meet the criteria for chemonucleolysis. Implantation can be performed similarly to the method described above and illustrated in FIGS. 2A-2H. For example, the patient can be worked up as if he or she would receive an injection of chymopapain in solution. For implantation, a hypodermic needle or a trocar/needle assembly with appropriate size (e.g., an inner diameter slightly larger than 1 mm) is inserted into the disc space until the needle tip passes through the outer and Inner annulus fibrosis to the center. Needle tip location can be verified using fluoroscopy. An appropriate length of implant is inserted into the trocar and a blunt stylet or other pushing device is used to push the rod forward until it is deposited near the center of the nuclear disc space. The trocar is then removed and the implant is left behind within the nucleus pulposus.

Figure 5:
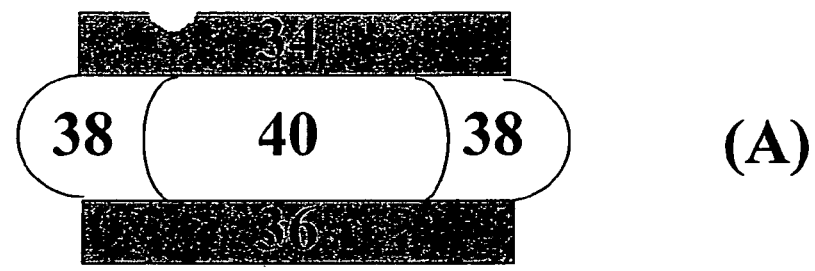
FIG. 5 illustrates the performance of an intervertebral disc implant as set forth in FIG. 2 after implantation into an intervertebral disc space.
Figure 5:
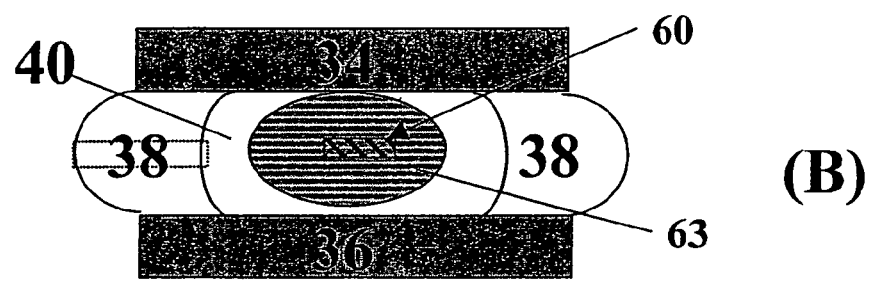
Figure 5:
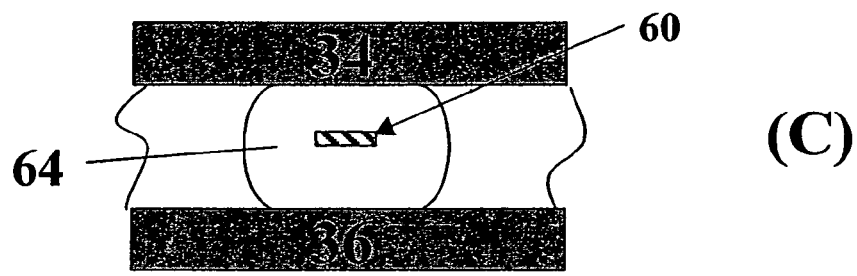
Figure 5:
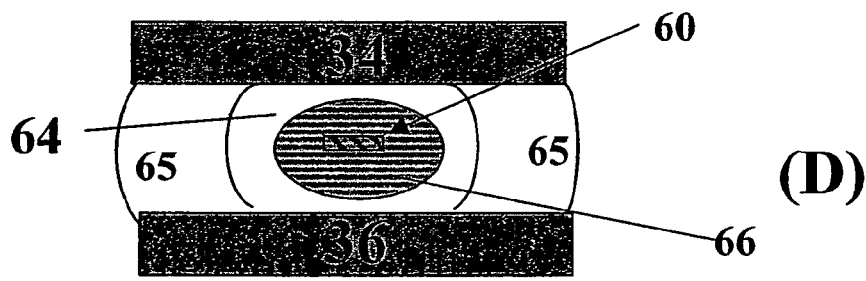
Figure 5:
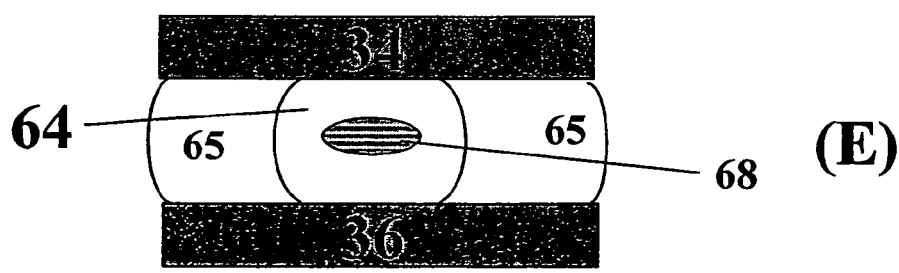

The performance of a device as set forth above after implantation into an intervertebral disc is illustrated in FIGS. 5A-5E. In FIG. 5A, a cross-sectional representation of two adjacent vertebrae 34, 36 and an intervertebral disc comprising an annulus fibrosus 38 and a nucleus pulposus 40 is shown. In FIG. 5B, a device 60 is shown implanted in the nucleus pulposus 40.

As set forth above, the device 60 is an elongate solid body comprising an inner core surrounded by a sheath. The core comprises growth factors and a first bioresorbable polymer and the sheath comprises chymopapain and a second bioresorbable polymer wherein the first polymer is absorbed at a slower rate than the second polymer. Since the faster resorbable polymer in the sheath absorbs water rapidly in the hydrated nucleus pulposus, the sheath swells up and releases chvmopapain to the surrounding disc tissues for proteolysis and rapidly erodes away (release phase I of 2).

Release phase I of the device is illustrated in FIGS. 5B and 5C. As shown in FIGS. 5B and 5C, the release 63 of the chemonucleolysis agent results in controlled degradation of the disc nucleus 64. The chemonucleolysis which occurs during release phase 1 can result in the reduction of intradiscal pressure and disc dehydration which can alleviate pain and sciatica.

As the sheath of the device is degraded, the core is exposed. The core of the device subsequently degrades and releases one or more growth factors 66, 68 to begin the disc repair/regeneration process (release phase 2 of 2). Release phase 2 is illustrated in FIGS. 5D and 5E. As shown in FIGS. 5D and 5E, the release of the growth factors 66, 68 into the nucleus during phase 2 can stimulate disc cells to repair or regenerate the disc 65 by synthesis of proteoglycan. This can help prevent, reduce or slow disc degeneration that may result from nucleolysis after treatment with a chemonucleolysis agent such as chymopapain. The core of the device is gradually eroded as shown in FIG. 5E and the device eventually disappears upon resorption.

Embodiment 14

Figure 6:
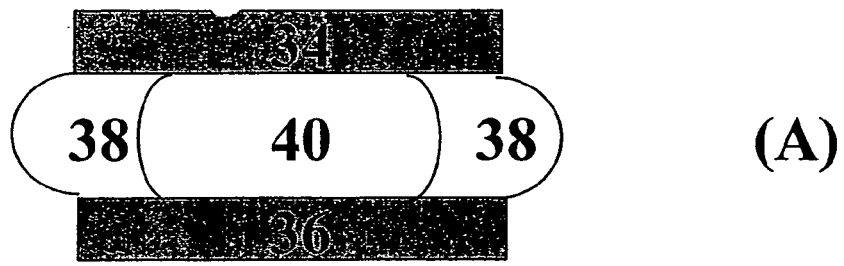
FIG. 6 illustrates a method of treating an intervertebral disc using an intervertebral disc implant as set forth in FIG. 2 wherein cells are injected into the disc space after chemonucleolysis is complete.
Figure 6:
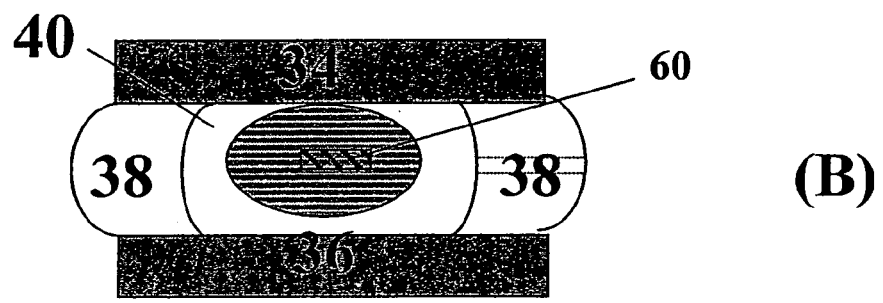
Figure 6:
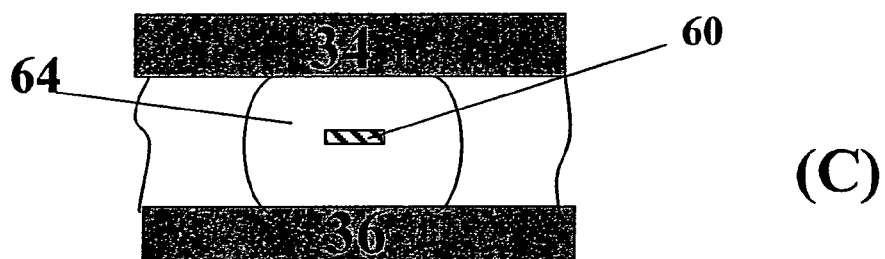
Figure 6:
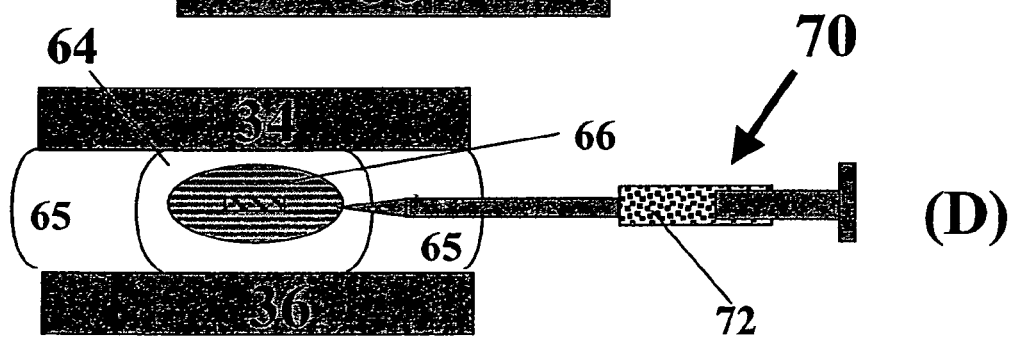
Figure 6:
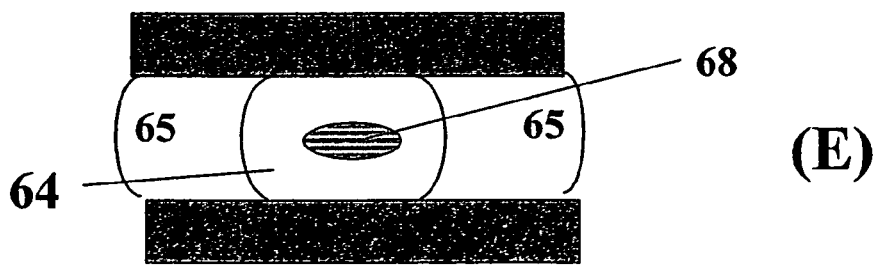

In this embodiment, the device described above in Embodiment 13 is implanted into the nucleus of a disc and notochordal cells are injected into the disc space during phase 2 of the release (i.e. during release of growth factors from the core of the device during the disc repair/regeneration phase). This process is illustrated in FIG. 6. In particular, as shown in FIG. 6D, cells 72 loaded in a syringe 70 can be injected into the nucleus during the release of the one or more growth factors 66. The cells can be injected after the completion of chymonucleolysis and/or during the release of the growth factor 66 for disc repair/regeneration. Depending on the device, this may up to a few weeks to a few months after implantation.

Embodiment 15

This embodiment is similar to Embodiment 14 except fibrochondrocyte (instead of notochordal) cells are injected into the disc space during release phase 2.

Embodiment 16

This embodiment is similar to Embodiment 15 except mesenchymal stem cells (instead of notochordal cells) are injected into the disc space during release phase 2.

Embodiment 17

This embodiment is similar to Embodiment 13 except pain medication is used as an active agent in the core of the device instead of growth factors. Implantation of this embodiment of the device allows for pain management following chemonucleolysis of the nucleus.

Embodiment 18

This embodiment is similar to Embodiment 13 except that both a pain medication and chymopapain are incorporated into the sheath of the device for simultaneous pain relief and chemonucleolysis during the first phase of release. One or more growth factors are incorporated into the core of the device.

Embodiment 19

This embodiment is similar to Embodiment 13 except that the device comprises three regions instead of two: a core, an inner sheath, and an outer sheath. According to one embodiment, pain medication can be incorporated into the outer sheath and a chemonucleolysis agent (e.g., chymopapain) can be incorporated into the inner sheath of the device. Growth factors can be incorporated into the core of the device.

Figure 7:
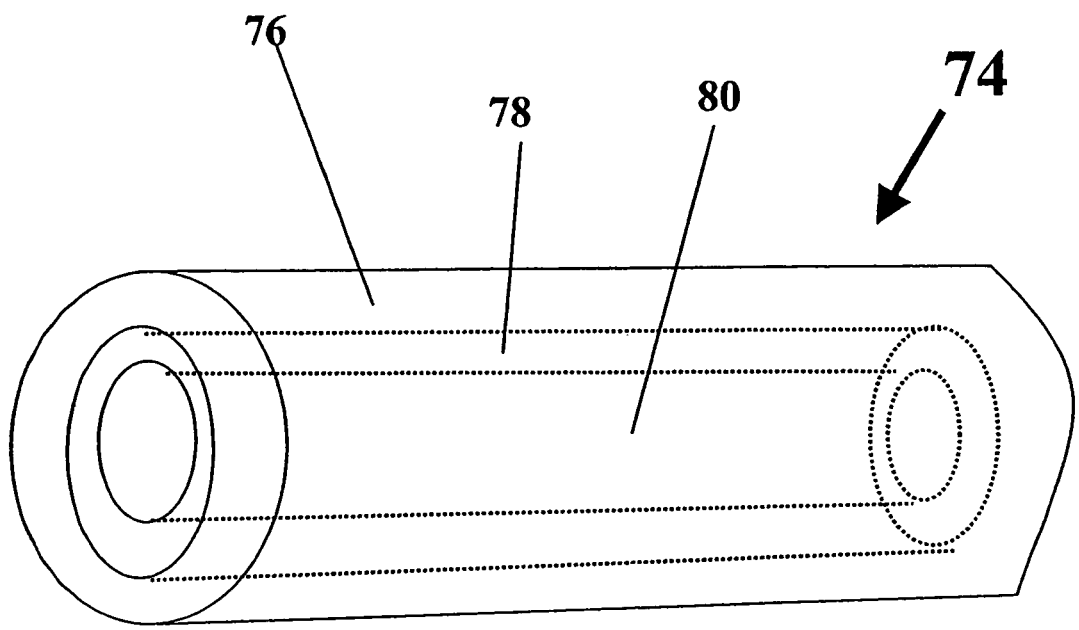
FIG. 7 illustrates an intervertebral disc implant for the delivery of multiple (i.e., three) active agents.

A device of his type is shown in FIG. 7. As shown in FIG. 7, the device 74 comprises a core 80, an inner sheath 78 and an outer sheath 76. This device has three release phases. During phase I of release, the active agent (e.g., a pain medication) is first released from the outer sheath. During phase 2, a chemonucleolysis agent (e.g., chymopapain) is released from the inner sheath for chemonucleolysis. During phase 3, one or more growth factors are released from the core for disc repair and regeneration.

Embodiment 20

This embodiment is similar to Embodiment 14 except the implanted devices are microspheres instead of elongate solid bodies. The microspheres can be suspended in solution (e.g., saline) and injected into the intervertebral disc space using a hypodermic needle.

Figure 8:
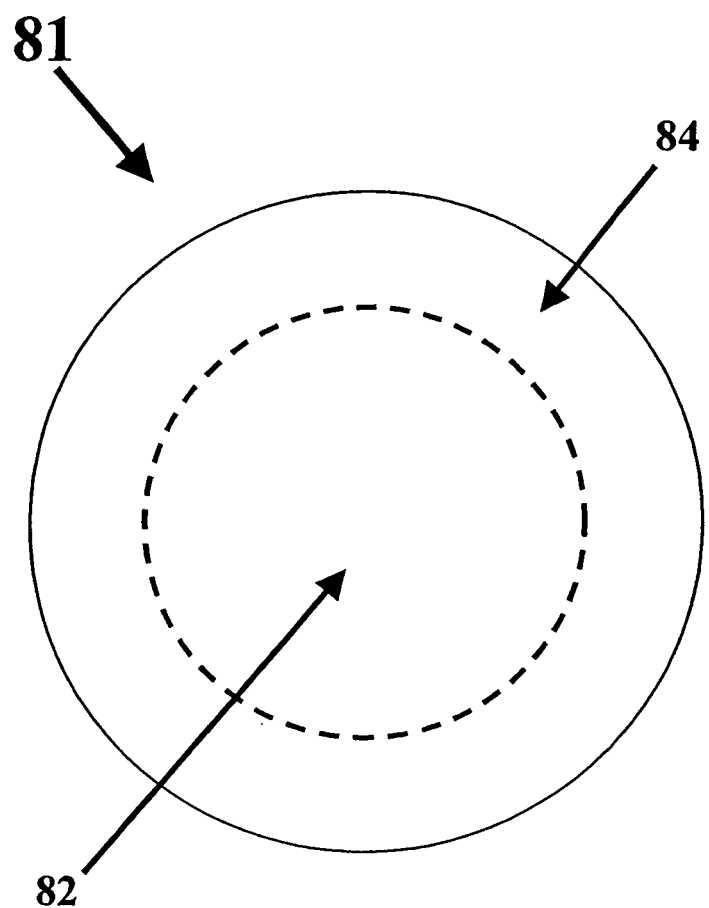
FIG. 8 shows a microsphere comprising a chemonucleolysis agent.

A microsphere comprising first and second active agents is shown in FIG. 8. As shown in FIG. 8, the microsphere 81 includes a core 82 comprising a first active agent and a shell 84 comprising a second active agent. According to an exemplary embodiment, the first active agent can be a growth factor and the second active agent can be a chemonucleolysis agent such as chymopapain.

Embodiment 21

This embodiment is similar to Embodiment 13 except that the sheath of the device comprises chymopapain and a temperature-sensitive bioresorbable hydrogel. As soon as the hydrogel comes into contact with body fluid at 37° C. within the disc nucleus, it undergoes a phase transformation to allow the release of chymopapain at a high rate for rapid chemonucleolysis.

Embodiment 22

This embodiment is similar to Embodiment 14 except that the core of the device that contains one or more growth factors comprises a pH-sensitive resorbable polymer binder. After chemonucleolysis, the polymer binder in the sheath degrades significantly and lowers the local pH. This change in pH triggers the core to release the one or more growth factors for disc repair and/or regeneration.

Embodiment 23

This embodiment is similar to Embodiment 14 except chondroitinase ABC is used instead of chymopapain as a chemonucleolysis agent.

Embodiment 24

This embodiment relates to the treatment of a "black" disc. In the case of a degenerated, dehydrated or "black" disc, chemonucleolysis is not necessary. A device suitable for the treatment of such a disc is provided which is similar to Embodiment 14 except that pain medication is used as an active agent in the sheath instead of chymopapain. Growth factors are included in the core for repair or regeneration of the disc. In an alternative embodiment, microspheres comprising pain medication in the shell and growth factors in the core can also be used. The microspheres can be implanted into an intervertebral disc using the technique illustrated in FIG. 9.

Figure 10:
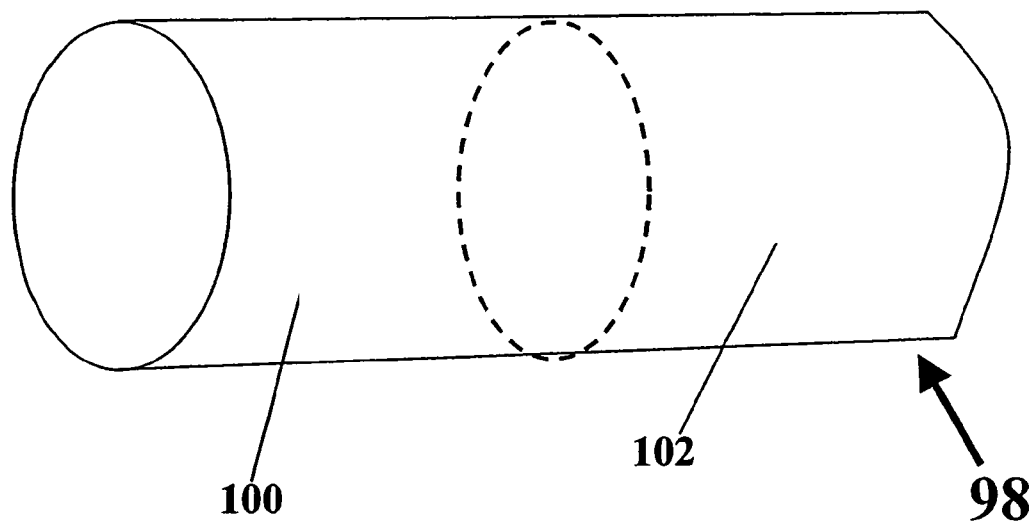
FIG. 10 illustrates an alternative embodiment of an intervertebral disc implant for the delivery of multiple (i.e., two) active agents.

Various alternative embodiments of devices comprising first and second active agents are shown in FIGS. 10-15. FIG. 10 illustrates an alternative embodiment of an intervertebral disc implant for the delivery of multiple (i.e., two) active agents. As shown in FIG. 10, the device 98 is an elongate solid body comprising a first region 100 and a second region 102 adjacent to the first region 100. The first region 100 can comprise a first active agent and the second region 102 can comprise a second active agent. Each of the regions 100, 102 can also comprise a binder. The binder in each of the regions can be the same or different. The binder in each region can be chosen to achieve the desired release characteristics for each active agent.

Figure 11:
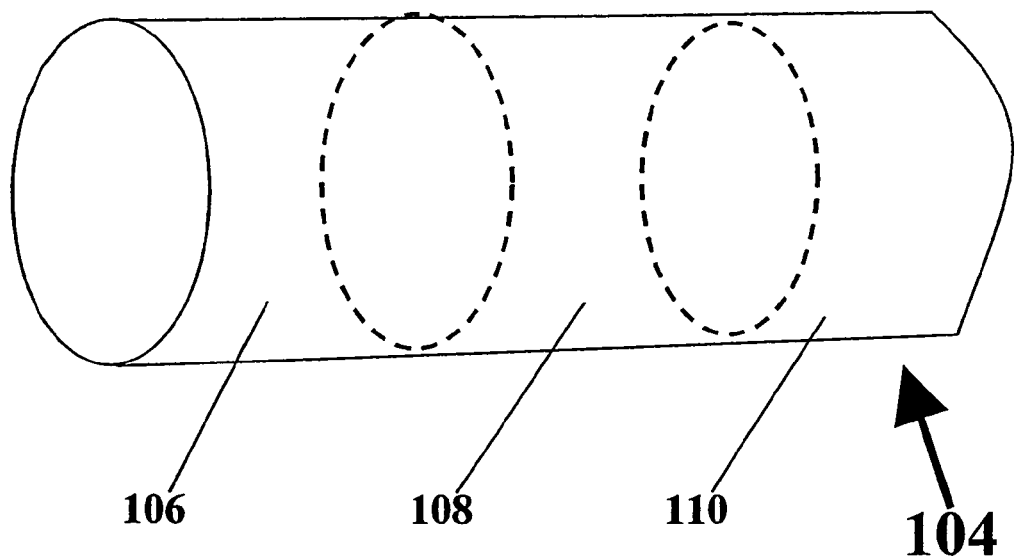
FIG. 11 illustrates an alternative embodiment of an intervertebral disc implant for the delivery of multiple (i.e., three) active agents.

FIG. 11 illustrates an alternative embodiment of an intervertebral disc implant for the delivery of multiple (i.e., three) active agents. As shown in FIG. 11, the device 104 is an elongate solid body comprising a first region 106, a second region 108 adjacent to the first region 106, and a third region 110 adjacent to the second region 108. The first region 106 can comprise a first active agent, the second region 108 can comprise a second active agent different than the first active agent, and the third region 110 can comprise a third active agent different than the first and second active agents. Each of the regions 106, 108, 110 can also comprise a binder. The binder in each of the regions 106, 108, 110 can be the same or different. The binder in each region 106, 108, 110 can be chosen to achieve the desired release characteristics for the active agent contained in that region.

Figure 12:
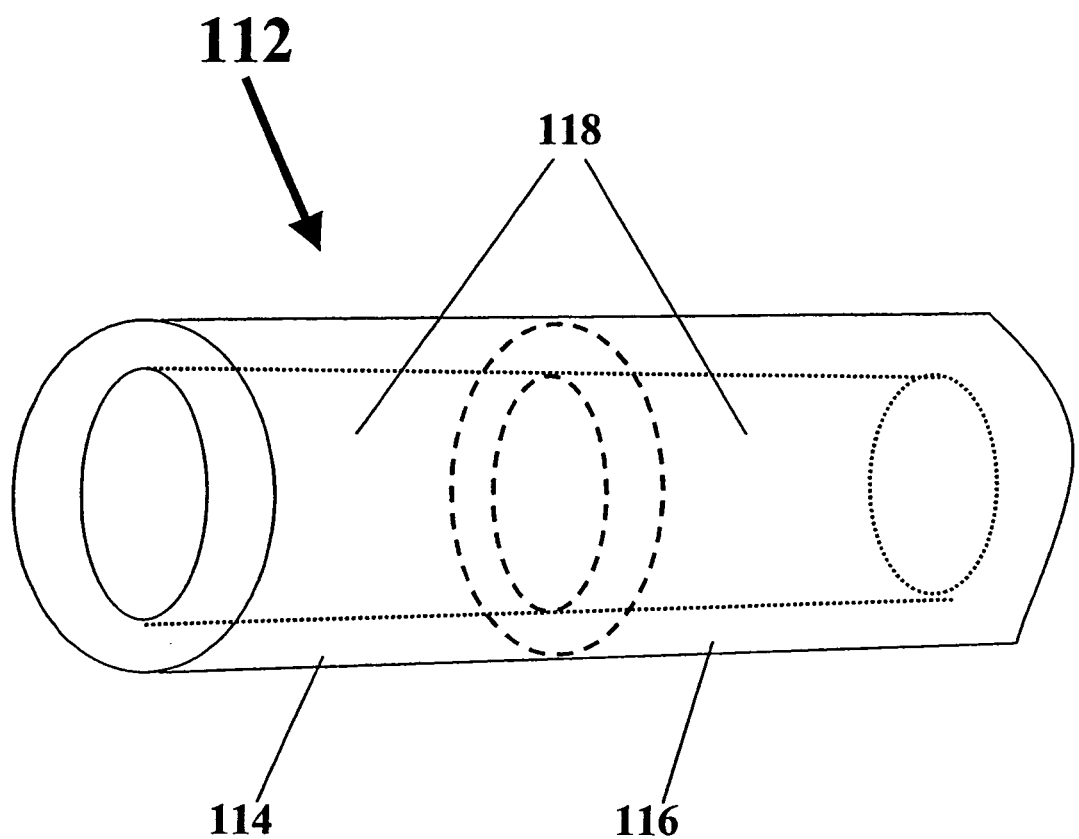
FIG. 12 illustrates an alternative embodiment of an intervertebral disc implant for the delivery of multiple (i.e., three) active agents having a sheath/core configuration wherein two of the active agents are in different portions of the sheath and the third active agent is in the core.

FIG. 12 illustrates an alternative embodiment of an intervertebral disc implant for the delivery of multiple (i.e., three) active agents. As shown in FIG. 12, the device 112 has a sheath/core configuration. The sheath comprises a first region 114 and a second region 116 each of which can comprise a different active agent. A third active agent is included in the core 118. Each of the regions 114, 116, 118 can also comprise a binder. The binder in each of the regions 114, 116, 118 can be the same or different. The binder in each region 114, 116, 118 can be chosen to achieve the desired release characteristics for each active agent.

Figure 13:
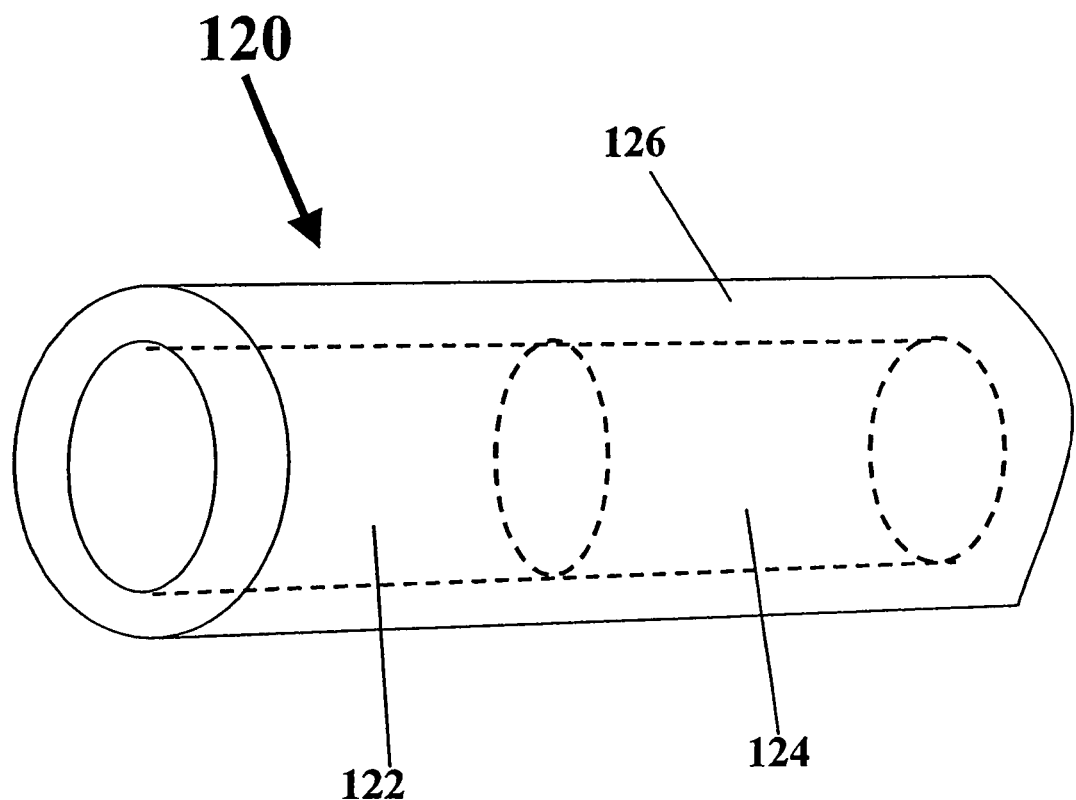
FIG. 13 illustrates an alternative embodiment of an intervertebral disc implant for the delivery of multiple (i.e., three) active agents having a sheath/core configuration wherein one of the active agents is in the sheath and the second and third active agents are in different portions of the core.

FIG. 13 illustrates an alternative embodiment of an intervertebral disc implant for the delivery of multiple (i.e., three) active agents. As shown in FIG. 13, the device 120 has a sheath/core configuration. The sheath 126 can comprise a first active agent. The core comprises a first region 122 and a second region 124 each of which can comprise a different active agent (e.g., second and third active agents, respectively). Each of the regions 122, 124, 126 can also comprise a binder. The binder in each of the regions 122, 124, 126 can be the same or different. The binder in each region 122, 124, 126 can be chosen to achieve the desired release characteristics for each active agent.

Figure 14:
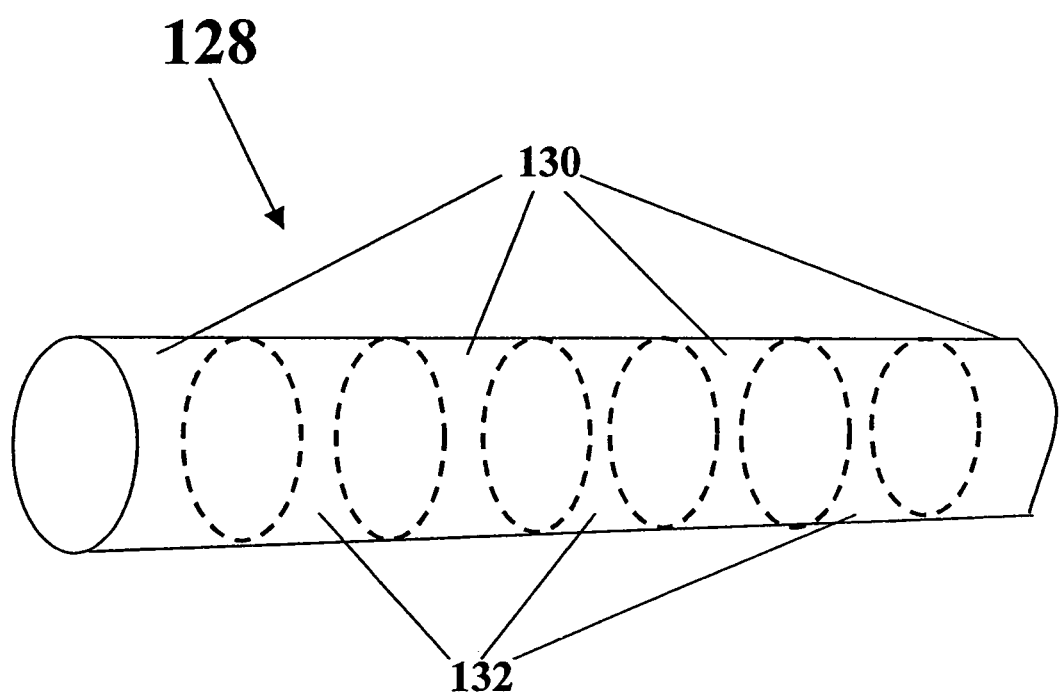
FIG. 14 illustrates an alternative embodiment of an intervertebral disc implant for the delivery of multiple (i.e., two) active agents having a rod configuration wherein alternating portions of the rod contain each of the two active agents.

FIG. 14 illustrates an alternative embodiment of an intervertebral disc implant for the delivery of multiple (i.e., two) active agents having an elongate configuration. As shown in FIG. 14, the device 128 comprises regions of a first active agent 130 alternating with regions of a second active agent 132. Each of the regions can also comprise a binder. The binder in each of regions 130 and regions 132 can be the same or different. The binder in each of regions 130 and regions 132 can be chosen to achieve the desired release characteristics for each active agent.

Figure 15:
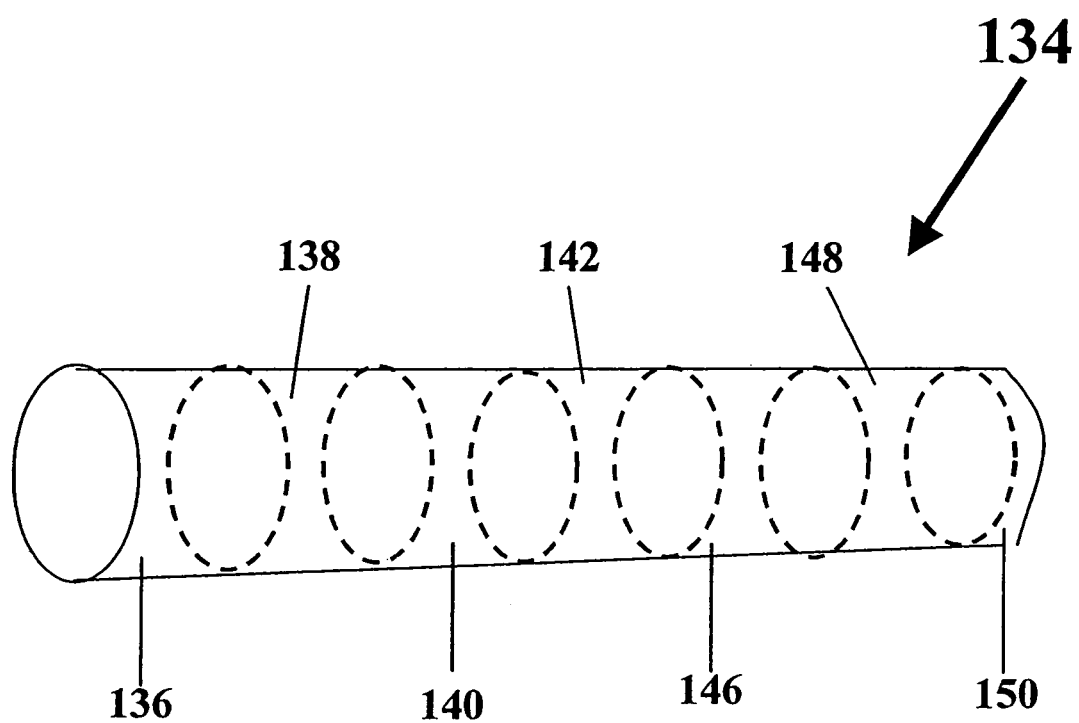
FIG. 15 illustrates an alternative embodiment of an intervertebral disc implant for the delivery of multiple active agents having a rod configuration wherein segments of the rod contain different active agents.

FIG. 15 illustrates an alternative embodiment of an intervertebral disc implant for the delivery of multiple active agents having an elongate configuration. As shown in FIG. 15, the device 134 comprises adjacent regions 136, 138, 140, 142, 144, 146, 148 each comprising a different active agent. Although seven regions are shown, devices having more or fewer regions can also be used. Each of the regions 136, 138, 140, 142, 144, 146, 148 can also comprise a binder. The binder in each of the regions 136, 138, 140, 142, 144, 146, 148 can be the same or different. The binder in each of the regions 136, 138, 140, 142, 144, 146, 148 can be chosen to achieve the desired release characteristics for each active agent.

The devices can have be of any shape and size suitable for implantation into the intervertebral space of a mammal. For example, the device can be an elongate solid body. According to one embodiment, the cross section of the elongate solid body can have a maximum dimension of five (5) mm or less. According to further embodiments, the cross section of the elongate solid body can have a maximum dimension of three (3) mm or less, two (2) mm or less, or one (1) mm or less. The phrase "maximum dimension" refers to the longest straight line that can be drawn on a given area. For example, the maximum dimension of a circle is its diameter. The cross-section of the device can be of any shape. For example, the cross section can be circular or polygonal (e.g., octagonal).

Figure 16A:
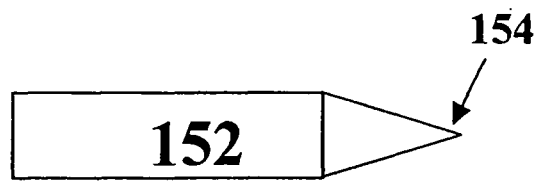
FIGS. 16A-16O illustrate various profile shapes for intervertebral disc implants.
Figure 16B:
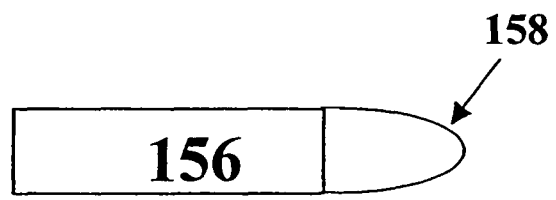
Figure 16C:
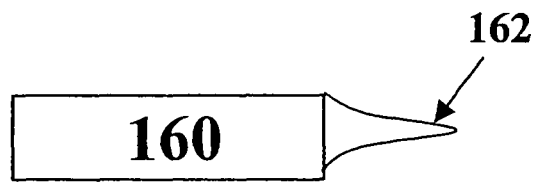
Figure 16D:
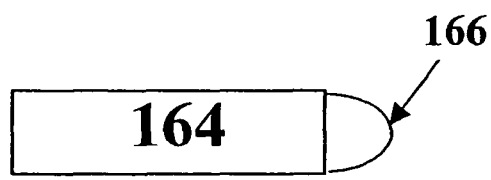
Figure 16E:
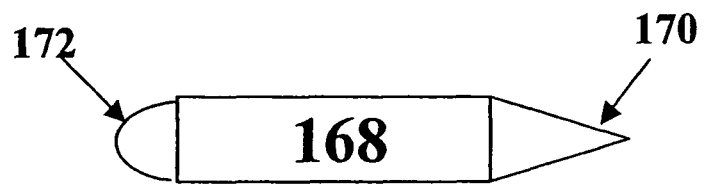
Figure 16F:
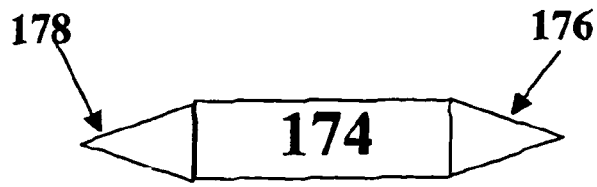
Figure 16G:
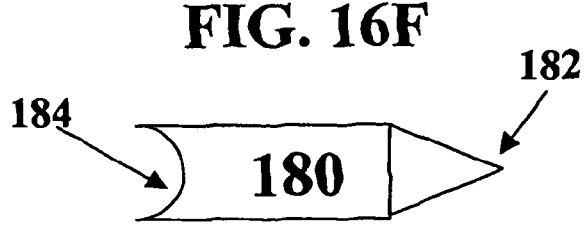
Figure 16H:
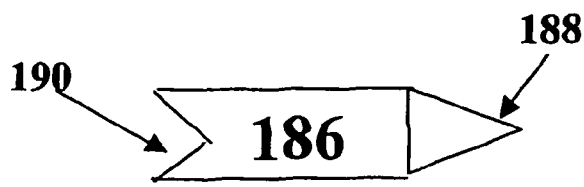
Figure 16I:
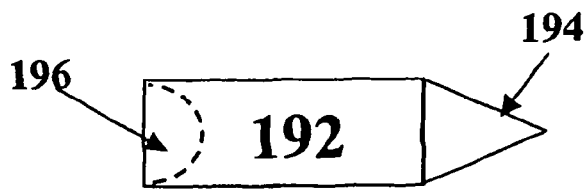
Figure 16J:
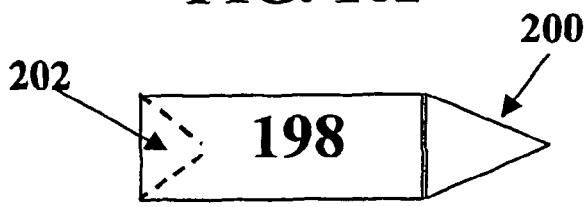
Figure 16K:
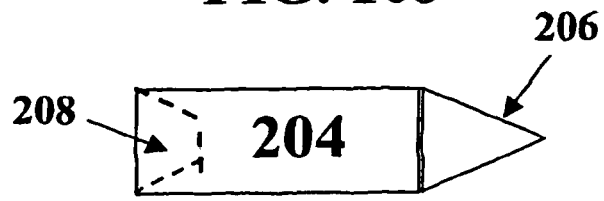

The shape and size of the implant can be chosen to achieve the desired release characteristics from the device. FIGS. 16A-16O illustrate various profile shapes for elongate solid body intervertebral disc implants. The insertion end of the device can be square (not shown). Alternatively, as shown in FIGS. 16B and 16D, the elongate solid body of the device 156, 164 can have a rounded insertion end 158, 166. Alternatively, as shown in FIGS. 16A, 16C and 16E-O the elongate solid body of the device 152, 160, 168, 174, 180, 186, 192, 198, 204, 210, 216, 222, 226 can have a tapered or pointed insertion end 154, 162, 170, 176, 182, 188, 194, 200, 206, 212, 218, 223, 227 The shape of the leading end can be chosen to facilitate implantation. For example, a tapered or rounded leading end can require less force to insert through a small aperture than a square leading end.

As shown in FIGS. 16A-16D, the end opposite the insertion end (i.e., the trailing end) of the elongate solid body of the device 152, 156, 160, 164 may be square. Alternatively, the trailing end of the elongate solid body may be rounded 172 or tapered 174 as shown in FIGS. 16E and 16F, respectively, or concave 184, 190, 196, 202, 208 as shown in FIGS. 16G-16K.

Figure 16L:
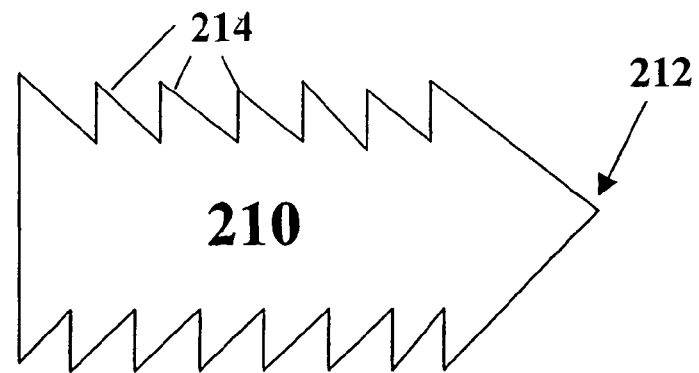
Figure 16M:
Figure 16N:
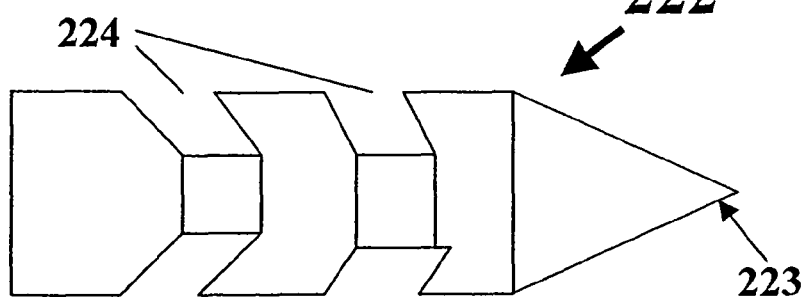
Figure 16O:
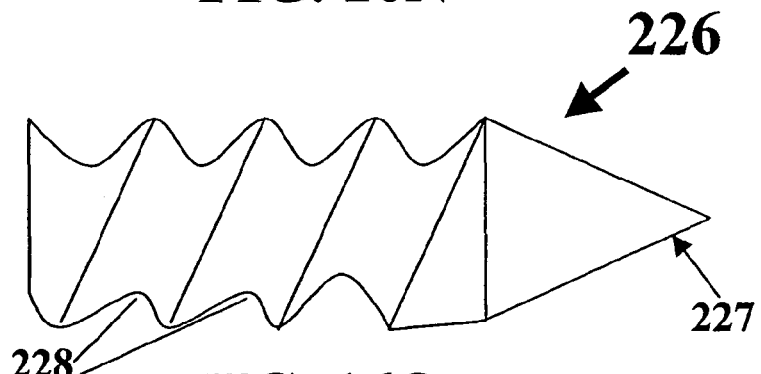

FIGS. 16L-16O are profile shapes of alternative elongate solid body implants. As shown in FIG. 16L, the implant 210 can have a tapered end 212 and a series of serrations 214 along its length. Alternatively, as shown in FIG. 16M, the implant 216 can have a tapered end 218 and a series of grooves 220 running down its length. As shown in FIG. 16N, an implant 222 having a tapered end 223 and a series of angled indentations 224 along its length is also provided. As shown in FIG. 16O, an implant 226 having a tapered end 222 and threads 228 running the length of the remainder of the solid body is also provided.

Figure 17:
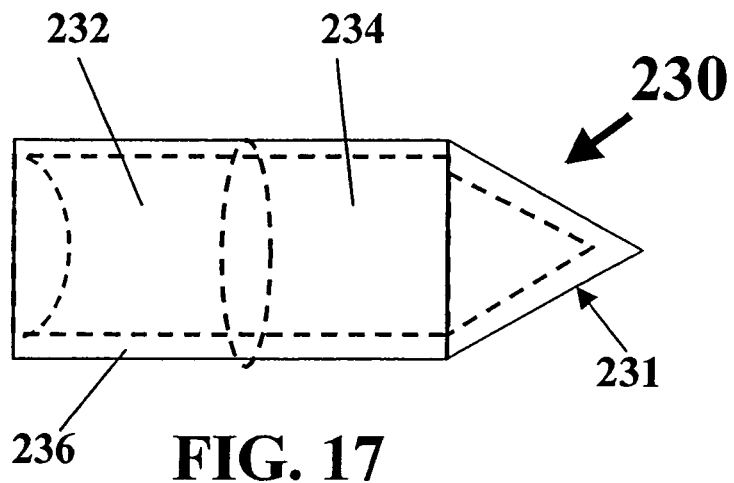
FIG. 17 illustrates an alternative embodiment of an intervertebral disc implant for the delivery of multiple (i.e., two) active agents having a rod configuration, a pointed insertion end and a hydrogel coating to provide lubricity.

FIG. 17 illustrates an alternative embodiment of an intervertebral disc implant 230 for the delivery of multiple (i.e., two) active agents. As shown in FIG. 17, the device 230 has an elongate configuration comprising two regions 232, 234 each of which contain a different active agent and a tapered insertion end 231. The device also has a coating 236 to provide lubricity. The coating 236 may be a hydrogel coating.

Figure 18:
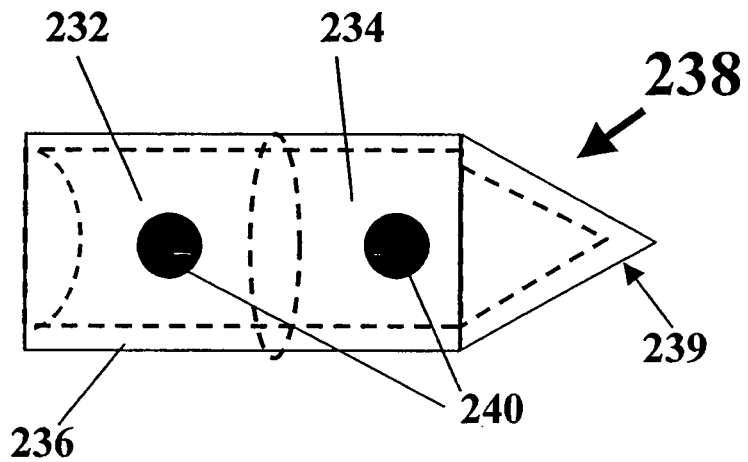
FIG. 18 illustrates an alternative embodiment of an intervertebral disc implant for the delivery of multiple (i.e., two) active agents having a rod configuration, a pointed insertion end, a hydrogel coating to provide lubricity and x-ray marker beads.

FIG. 18 illustrates an alternative embodiment of an intervertebral disc implant for the delivery of multiple (i.e., two) active agents. As shown in FIG. 18, the device 238 has an elongate configuration, a pointed insertion end 239, and a coating 236 to provide lubricity. The device also comprises x-ray markers 240 (two shown). As shown in FIG. 18, the x-ray markers 240 are beads. As also shown in FIG. 18, each of the regions of the device 232, 234 comprises a marker 240. The x-ray markers 240 can comprise a material detectable by x-ray. Exemplary materials for the x-ray markers 240 include, but are not limited to, barium sulfate, platinum and tantalum.

Figure 19:
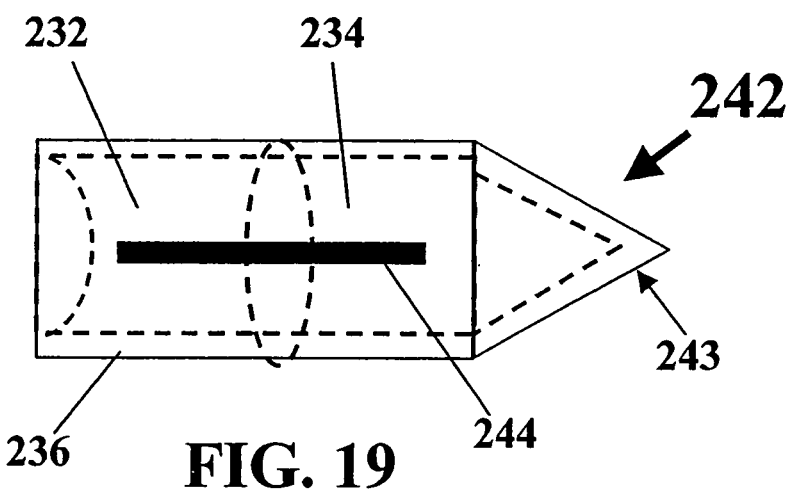
FIG. 19 illustrates an alternative embodiment of an intervertebral disc implant for the delivery of multiple (i.e., two) active agents having a rod configuration, a pointed insertion end, a hydrogel coating to provide lubricity and an x-ray marker thread.

FIG. 19 illustrates an alternative embodiment of an intervertebral disc implant for the delivery, of multiple (i.e., two) active agents. As shown in FIG. 19, the device 242 has an elongate configuration, a pointed insertion end 243, and a coating 236 to provide lubricity. The device also has an x-ray marker 244 in the form of a thread. The x-ray marker 244 can comprise a material detectable by x-ray. Exemplary materials for the x-ray marker 244 include, but are not limited to, barium sulfate, platinum and tantalum.

Figure 20A:
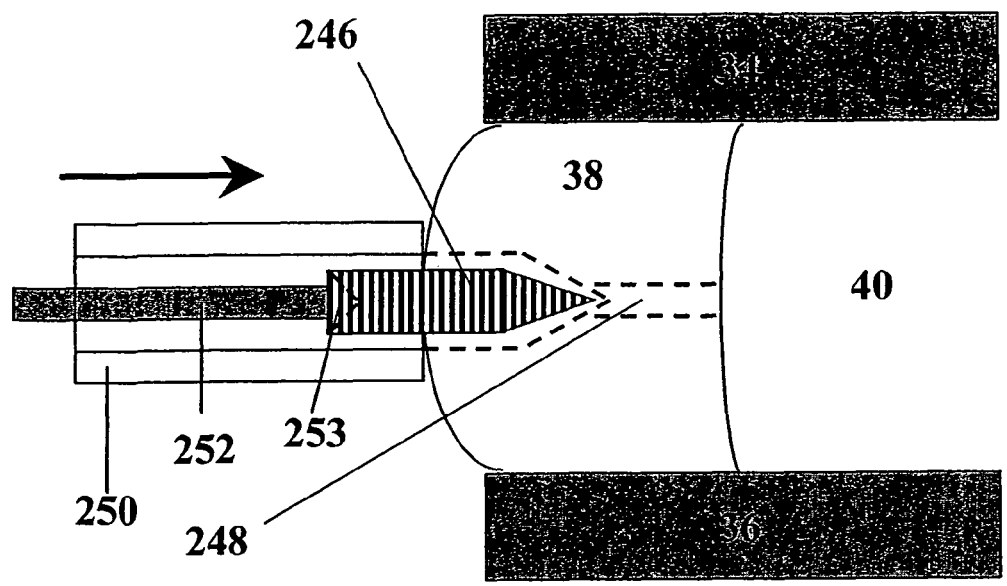
FIGS. 20A and 20B illustrate a method of implanting an intervertebral disc implant as shown in FIGS. 20A-200.
Figure 20B:
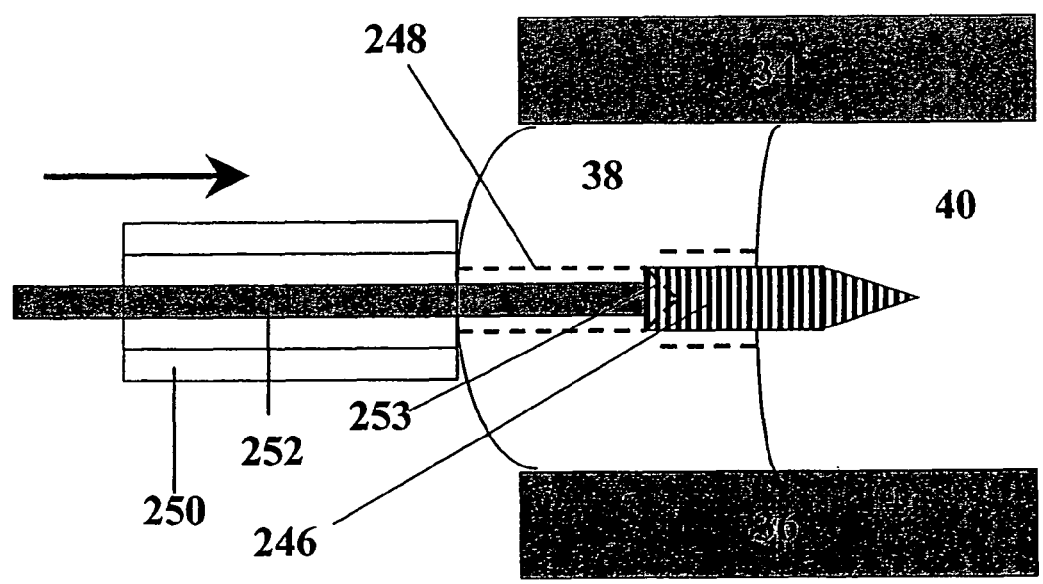

FIGS. 20A and 20B illustrate a method of implanting an intervertebral disc implant of the type shown in FIGS. 16A-16O. As shown in FIG. 20A, an aperture 248 is made through the annulus 38 and into the nucleus 40 of an intervertebral disc. A hollow tube 250 (e.g., a trocar) having an internal diameter slightly larger than the outer diameter of the device 246 being implanted is then placed into contact with the annulus 38 such that the end of the tube 250 is over the aperture 248. The implant 246 is placed in the tube and pushed through the aperture and into the nucleus 40 as shown in FIG. 20B. Insertion of the device 246 can be accomplished using a pushing device 252 such as a blunted needle or a stylet or a puch rod.

The implant shown in FIGS. 20A and 20B has a concave trailing end 253. The concave trailing end 253 helps to keep the pushing device engaged in the implant 246 as the implant 246 is being inserted into the nucleus 40.

As shown in FIG. 20B, during insertion, the tissues surrounding the aperture 248 collapse behind the inserted device 246 thereby partially closing the dilated aperture 248. After insertion, the pushing device 252 is removed (not shown) thereby leaving behind an aperture in the annulus that is significantly smaller than the diameter of the device inserted. Insertion of a device larger than the aperture is possible due to the viscoelastic nature of the annular tissue and the very short times involved in the dilation/insertion step.

Exemplary active agents which can be incorporated into the devices include, but are not limited to:

chemonucleolysis agents such as chymopapain, collagenase, chondroitinase-ABC and human proteolytic enzymes;

pain medications such as codeine, propoxyphene, hydrocodone, and oxycodone; and growth factors such as transforming growth factor β proteins, bone morphogenetic proteins, fibroblast growth factors, platelet-derived growth factors, and insulin-like growth factors.

Any of the aforementioned active agents or combinations thereof can be incorporated into the device.

Examples of binders or matrix materials include, but are not limited to:

non-resorbable polymers such as poly(urethanes), poly(siloxanes), poly(methyl methacrylate), poly(ethylene), poly(vinyl alcohol, poly(vinyl pyrrolidon), poly(2-hydroxy ethyl methacrylate), poly(acrylic acid), poly(ethylene-co-vinyl acetate, poly(ethylene glycol), poly(methacrylic acid), and polyacrylamide;

bioresorbable polymers such as polylactides (PLA), polyglycolides (PGA), poly(lactide-co-glycolides) (PLGA), polyanhydrides, and polyorthoesters; and natural polymers such as: polysaccharides, collagens, silk, elastin, keratin, albumin, and fibrin.

Any combination of the above binders can be used in the device.

When a growth factor is included in the device, various types of cells can be injected into the disc space during the growth factor releasing phase of the device in order to promote disc repair and regeneration. Exemplary cells that can be injected into the intervertebral disc during the growth-factor-releasing phase of the device include, but are not limited to, notochords, fibrochrondrocytes, and mesenchymal stem cells. The cells can be modified with a growth factor. For example, the cells can be transfected with a nucleic acid (e.g., an expression vector) encoding a growth factor such as a bone morphogenetic protein or a LIM mineralization protein.

As set forth above, the intervertebral disc implant can be formed by consolidating an admixture comprising a binder and one or more active agents into a solid body. Alternatively, the intervertebral disc implant can include a plurality of particles at least some of which comprise an active agent wherein the particles are unconsolidated (i.e., in loose admixture). The implant comprising particulate material can be implanted into an intervertebral disc using a hollow tube (e.g., a trocar) as a delivery device. The implant can further include particles comprising a binder. The particles comprising a binder can be mixed with the particles comprising the active agent to facilitate handling and delivery of the particulate material into the disc nucleus.

According to a further embodiment, at least some of the individual particles in the implant can comprise an active agent and a binder. Particles comprising an active agent and a binder can be made by mixing together particles of the active agent and the binder, forming a consolidated solid body from the admixture (e.g., using heat and/or pressure), and comminuting the solid body to form particles of the desired size.

An implant comprising a plurality of particles wherein at least some of the particles comprise a first active agent and at least some of the particles comprise a second active agent is also provided. The implant according to this embodiment can further comprise a binder. The implant can be made by mixing particles of the first and second active agents with particles of the binder to form an implant. Alternatively, an admixture of first and second active agents and binder can be consolidated into a solid body and comminuted into particles to form the implant. According to this embodiment, individual particles in the implant comprise the first and second active agents as well as the binder. Implants comprising additional active agents (i.e., three or more) can also be made using the techniques described above.

For either the solid body (e.g., consolidated) implants or the particulate (e.g., non-consolidated) implants, the particles comprising active agent(s) in the implant can be sized to achieve a desired release profile. Smaller particles have a higher surface area and will therefore typically result in more rapid release of the active agent. According to one embodiment, the particles of active agent(s) in the implant can have an average diameter of 0.1 to 500 μm. According to further exemplary embodiments, the particles of active agent in the implant can have an average diameter of from 0.5 to 250 pm or from 1 to 100 μm. When the implant is a solid body including multiple regions each comprising a different active agent, active agents having different particle sizes can be used in each region of the implant to achieve the desired release characteristics for that active agent.

If a binder is used, the amount of binder in the implant can also be varied to achieve the desired release characteristics for the active agent(s) in the implant. In the case of particulate implants, the amount of binder can also be varied to achieve the desired handling characteristics for the particulate material. According to a first exemplary embodiment, the implant can comprise from 10 to 100% by volume of the active agent with the remainder (i.e., 0 to 90% by volume) being binder. According to a further exemplary embodiment, the implant can comprise from 25 to 75% by volume of the active agent with the remainder (i.e., 25 to 75 by volume) being binder. When the implant is a solid body including multiple regions each comprising a different active agent, different amounts of binder can be used in each region of the implant to achieve the desired release characteristics for that active agent.

EXPERIMENTAL

Below is a summary of an experiment involving the implantation of a device comprising chymopapain as a chemonucleolysis agent and collagen as a binder.

Materials
   Chymopapain powder
   Fascian allogenic collagen
   Saline

Methods
   Three thoracic or lumbar pig discs were used in this experiment. One disc remained untreated as the control.

A second disc was injected with approximately 0.003 g of hymopapain powder in 0.7 cc saline.

An implant according to an embodiment of the invention comprising an unconsolidated mixture of chymopapain powder and a binder was implanted into a third disc. The implant included approximately 0.003 g of chymopapain powder mixed with collagen powder (5:1 collagen/chymopapain approximate volume ratio).

Figure 21A:
FIGS. 21 A-21 C are pictures of pig discs wherein FIG. 21 A is a picture of an untreated control disc, FIG. 21 B is a picture of a disc treated with chymopapain in saline solution, and FIG. 21 C is a picture of disc treated with an implant according to one embodiment of the invention comprising chymopapain and collagen powder.
Figure 21B:
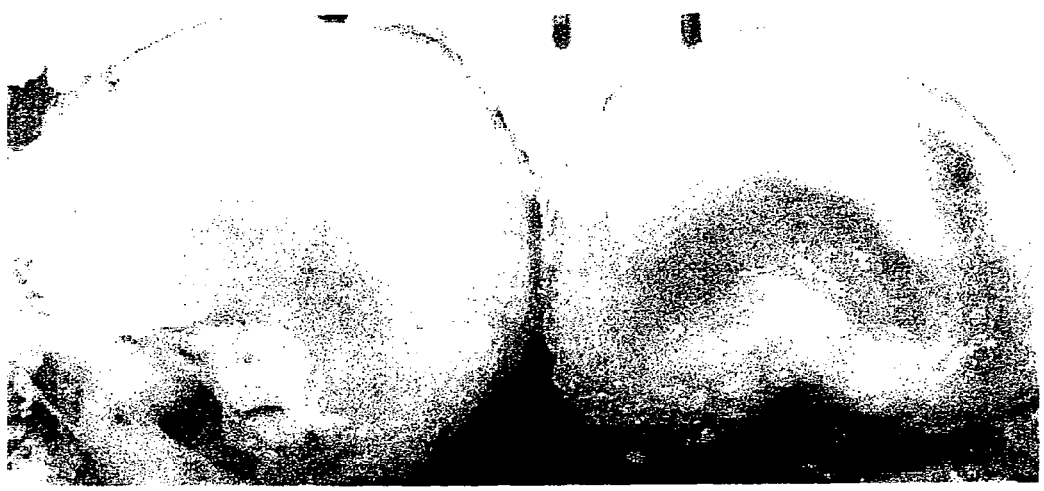
Figure 21C:

Each of the discs were left in a refrigerator for approximately 5 days before sectioning for observation. Pictures of sections of each disc were then taken. FIG. 21A is a picture of the control disc. FIG. 21B is a picture of the second disc. FIG. 21 C is a picture of the third disc.

Results and Discussion
   As can be seen from FIG. 21B, the nucleus pulposus of the disc treated with chymopapain solution appeared as a viscous liquid plus gel mixture which was significantly more flowable compared to the gelatinous consistency of the nucleus of the control disc (FIG. 21 A). This is probably due to the breakdown of the nucleus pulposus matrix as well as the presence of the original injected liquid. In addition, leakage of the injected chymopapain solution was observed at the injection site of the annulus fibrosis. This is most likely a result of the high intradiscal pressure, which was exacerbated by the injected liquid. Clinical complications that are associated with injection of chymopapain in chemonucleolysis are probably attributed, in part, to this observed leakage.

As can be seen from FIG. 21 C, The nucleus pulposus of the disc treated with the implant comprising chymopapain powder appeared to have the same consistency as that of the control disc (FIG. 21 A) but with noticeably smaller volume. Further, the inserted device had almost completely disappeared.

The chymopapain powder also appeared to break down the added collagen. Although it was expected that, in powder form, chymopapain would work more slowly in breaking down the nucleus pulposus, the presence of significant quantities of added collagen may have interfered with the proteolytic action of chymopapain on the nucleus.

The above observations show that chymopapain in solution form works rapidly in breaking down the nucleus pulposus while implantation of a solid device comprising chymopapain in solid form (e.g., in powder form) works more slowly. Without wishing to be bound by theory, it is believed that the slower action of the solid implant results from diffusion control of the chymopapain. The above observations also show that, by using an implant comprising a chemonucleolysis agent in solid form, localized degradation of the disc nucleus can be achieved.

As a result of this study, it can be clearly seen that chymopapain in solid form, when delivered to the nucleus pulposus in the form of a controlled release device, can help prevent or minimize complications associated with the leakage of chymopapain resulting from direct injection of chymopapain in solution.

While the foregoing specification teaches the principles of the present invention, with examples provided for the purpose of illustration, it will be appreciated by one skilled in the art from reading this disclosure that various changes in form and detail can be made without departing from the true scope of the invention.

What is claimed is:

1. An intervertebral disc implant comprising a chemonucleolysis agent in solid powder form, a plurality of particles and a binder, wherein the implant has a solid body throughout the cross-section of the implant and when placed into the nucleus pulposus of an intervertebral disc, the implant having a sheath comprising the chemonucleolysis agent incorporated into the sheath, the implant sustainably releases the chemonucleolysis agent into the nuclear disc tissue surrounding the implant to proteolytically degrade the tissue, the chemonucleolysis agent comprises chymopapain and is incorporated into the particles.

2. The intervertebral disc implant of claim 1, wherein the particles have an average diameter of 0.1 to 500 μm.

3. The intervertebral disc implant of claim 1, wherein the particles have an average diameter of 0.5 to 250 μm.

4. The intervertebral disc implant of claim 1, wherein the particles have an average diameter of 1 to 100 μm.

5. The intervertebral disc implant of claim 1, wherein the chemonucleolysis agent further comprises collagenase, chondroitinase-ABC and human proteolytic enzymes.

6. The intervertebral disc implant of claim 1, wherein the solid body is an elongate solid body.

7. The intervertebral disc implant of claim 1, wherein the solid body is an elongate solid body having a tapered or rounded end.

8. The intervertebral disc implant of claim 1, wherein the solid body is a microsphere.

9. The intervertebral disc implant of claim 1, wherein the solid body has a profile shape selected from the group consisting of the profile shapes depicted in FIGS. 16A, 16B, 16C, 16D, 16E, 16F, 16G, 16H, 16I, 16J, 16K, 16L, 16M, 16N and 16O.

10. The intervertebral disc implant of claim 1, wherein the solid body has a circular cross section.

11. The intervertebral disc implant of claim 1, wherein the implant comprises up to 90% by volume of the binder.

12. The intervertebral disc implant of claim 1, wherein the implant comprises from 25 to 75% by volume of the binder.

13. The intervertebral disc implant of claim 1, wherein the binder is a polymer.

14. The intervertebral disc implant of claim 1, wherein the binder is a non-resorbable polymer, a bioresorbable polymer, or a naturally occurring polymer.

15. The intervertebral disc implant of claim 1, wherein the binder is a non-resorbable polymer selected from the group consisting of polyurethanes, polysiloxanes, polymethyl methacrylate, polyethylene, polyvinyl alcohol, polyvinyl pyrrolidone, poly(2-hydroxy ethyl methacrylate), polyacrylic acid, poly(ethylene-co-vinyl acetate), polyethylene glycol, polymethacrylic acid, and polyacrylamide.

16. The intervertebral disc implant of claim 1, wherein the binder is a bioresorbable polymer selected from the group consisting of polylactides, polyglycolides, polylactide-co-glycolides, polyanhydrides, and polyorthoesters.

17. The intervertebral disc implant of claim 1, wherein the binder is a naturally occurring polymer selected from the group consisting of polysaccharides, collagens, silk, elastin, keratin, albumin, and fibrin.

18. The intervertebral disc implant of claim 1, wherein the implant further comprises a second active agent different than the chemonucleolysis agent.

19. The intervertebral disc implant of claim 18, wherein the second active agent is a pain medication or a growth factor.

20. The intervertebral disc implant of claim 18, wherein the second active agent is a pain medication selected from the group consisting of codeine, propoxyphene, hydrocodone, and oxycodone.

21. The intervertebral disc implant of claim 18, wherein the second active agent is a growth factor selected from the group consisting of a transforming growth factor-B protein, a bone morphogenetic protein, a fibroblast growth factor, a platelet-derived growth factor, and an insulin-like growth factor.

22. The implant of claim 1, wherein the solid body further comprises a hydrogel coating.

23. The implant of claim 1, further comprising an x-ray marker.

24. The implant of claim 23, wherein the x-ray marker is a bead or a thread.

25. The implant of claim 23, wherein the x-ray marker comprises barium sulfate, platinum or tantalum.

26. The implant of claim 6, wherein the elongate solid body has no cross-sectional area with a maximum dimension greater than 5 mm.

27. The implant of claim 6, wherein the elongate solid body has no cross-sectional area with a maximum dimension greater than 3 mm.

28. The implant of claim 6, wherein the elongate solid body has no cross-sectional area with a maximum dimension greater than 1 mm.

29. The implant of claim 1, wherein the implant erodes upon resorption.

* * * * *